US008173627B2

(12) United States Patent
Yoo

(10) Patent No.: US 8,173,627 B2
(45) Date of Patent: May 8, 2012

(54) NEUROPROTECTIVE EFFECT OF SOLUBILIZED UDCA IN FOCAL ISCHEMIC MODEL

(76) Inventor: Seo Hong Yoo, Wyckoff, NJ (US)

( * ) Notice: Subject to any disclaimer, the term of this patent is extended or adjusted under 35 U.S.C. 154(b) by 0 days.

(21) Appl. No.: 11/215,701

(22) Filed: Aug. 30, 2005

(65) Prior Publication Data

US 2006/0051319 A1    Mar. 9, 2006

Related U.S. Application Data

(60) Provisional application No. 60/605,566, filed on Aug. 30, 2004, provisional application No. 60/629,998, filed on Nov. 22, 2004.

(51) Int. Cl.
*A61K 31/575* (2006.01)
*C07J 9/00* (2006.01)

(52) U.S. Cl. .................. 514/182; 552/551

(58) Field of Classification Search .............. None
See application file for complete search history.

(56) References Cited

U.S. PATENT DOCUMENTS

| | | | |
|---|---|---|---|
| 3,845,770 A | 11/1974 | Theeeuwes et al. | 128/260 |
| 3,916,899 A | 11/1975 | Theeuwes et al. | 128/260 |
| 4,036,954 A | 7/1977 | Murakami et al. | 424/176 |
| 4,092,428 A | 5/1978 | Murakami et al. | 424/317 |
| 4,113,882 A | 9/1978 | Okazaki et al. | 424/317 |
| 4,320,146 A | 3/1982 | Walser | 424/319 |
| 4,327,725 A | 5/1982 | Cortese et al. | 128/260 |
| 4,585,790 A | 4/1986 | Padfield et al. | 514/471 |
| 4,681,876 A | 7/1987 | Marples et al. | 514/182 |
| 4,879,303 A | 11/1989 | Davison et al. | 514/356 |
| 5,057,321 A | 10/1991 | Edgren et al. | 424/413 |
| 5,149,537 A | 9/1992 | Azria et al. | 424/436 |
| 5,157,022 A | 10/1992 | Barbul | 514/18 |
| 5,260,074 A | 11/1993 | Sipos | 424/497 |
| 5,292,534 A | 3/1994 | Valentine et al. | 424/451 |
| 5,300,300 A | 4/1994 | Egidio et al. | 424/456 |
| 5,302,398 A | 4/1994 | Egidio et al. | 424/474 |
| 5,302,400 A | 4/1994 | Sipos | 424/494 |
| 5,310,560 A | 5/1994 | Widauer | 424/451 |
| 5,324,514 A | 6/1994 | Sipos | 424/94.63 |
| 5,342,625 A | 8/1994 | Hauer et al. | 424/455 |
| 5,380,533 A | 1/1995 | Egidio et al. | 424/456 |
| 5,446,026 A | 8/1995 | Ruff et al. | 514/15 |
| 5,470,581 A | 11/1995 | Grillo et al. | 424/479 |
| 5,484,776 A | 1/1996 | Racz et al. | 514/54 |
| 5,516,523 A | 5/1996 | Heiber et al. | 424/435 |
| 5,534,505 A | 7/1996 | Widauer | 514/169 |
| 5,578,304 A | 11/1996 | Sipos | 424/94.1 |
| 5,599,926 A | 2/1997 | Still et al. | 540/456 |
| 5,641,767 A | 6/1997 | Wess et al. | 514/172 |
| 5,653,987 A | 8/1997 | Modi et al. | 424/400 |
| 5,686,588 A | 11/1997 | Yoo | 536/13.3 |
| 5,750,104 A | 5/1998 | Sipos | 424/94.21 |
| 5,750,707 A | 5/1998 | Spargo | 546/321 |
| 5,843,929 A | 12/1998 | Larson et al. | 514/182 |
| 5,846,964 A | 12/1998 | Ozeki | 514/182 |
| 5,858,998 A | 1/1999 | Leuschner | 514/171 |
| 5,863,550 A | 1/1999 | Maeda et al. | 424/423 |
| 5,898,028 A | 4/1999 | Jensen et al. | 514/4 |
| 5,945,411 A | 8/1999 | Larson et al. | 514/171 |
| 5,965,164 A | 10/1999 | Fuisz et al. | 424/489 |
| 5,977,070 A | 11/1999 | Piazza et al. | 514/12 |
| 6,099,859 A | 8/2000 | Cheng et al. | 424/464 |
| 6,210,699 B1 | 4/2001 | Acharya et al. | 424/435 |
| 6,245,753 B1 | 6/2001 | Byun et al. | 514/56 |
| 6,251,428 B1 * | 6/2001 | Yoo | 424/455 |
| 6,309,663 B1 | 10/2001 | Patel et al. | 424/450 |
| 6,635,628 B2 | 10/2003 | Bouscarel et al. | 514/171 |
| 7,034,006 B2 * | 4/2006 | Yedgar et al. | 514/42 |
| 7,166,299 B2 | 1/2007 | Yoo | 424/455 |
| 7,303,768 B2 | 12/2007 | Yoo | 424/528 |
| 2001/0011146 A1 | 8/2001 | Joh et al. | 564/218 |
| 2001/0046521 A1 | 11/2001 | Zasloff et al. | 424/649 |
| 2002/0031558 A1 | 3/2002 | Yoo | 424/653 |
| 2002/0081361 A1 | 6/2002 | Towb et al. | 426/548 |
| 2003/0044413 A1 | 3/2003 | Steer et al. | 424/145.1 |
| 2005/0158408 A1 | 7/2005 | Yoo | 424/728 |
| 2006/0051319 A1 | 3/2006 | Yoo | 424/85.1 |
| 2006/0089331 A1 | 4/2006 | Yoo | 514/58 |
| 2006/0142241 A1 | 6/2006 | Yoo | 514/59 |
| 2006/0188530 A1 | 8/2006 | Yoo | 424/400 |
| 2007/0072828 A1 | 3/2007 | Yoo | 514/60 |

FOREIGN PATENT DOCUMENTS

CN    1450914    10/2003

(Continued)

OTHER PUBLICATIONS

Rodrigues et al., "Neuroprotection by a Bile Acid in an Acute Stroke Model in the Rat" Journal of Cerebral Blood Flow and Metabolism (2002) vol. 22, pp. 463-471.*
Ikeda et al., "Antioxidant Nutrients and hypoxia/ischemia brain injury in rodents" Toxicology (2003) vol. 189, pp. 55-61.*
Tanahashi et al., "Treatment of Acute Ischemic Stroke: Recent Progress" Internal Medicine (2002) vol. 41, pp. 337-344.*
2006 Chemical Abstracts Catalog, published 2006 by Chemical Abstracts Service, p. 52.*
Wardlaw et al., "Thrombolysis for acute ischaemic stroke (Review)" Cochrane Database of Systematic Reviews (2003), Issue 3, pp. 1-98.*
MacWalter et al., "A Benefit-Risk Assessment of Agents Used in the Secondary Prevention of Stroke" Drug Safety (2002) vol. 25 No. 13, pp. 943-963.*
The Merck Manual of Diagnosis and Therapy, published 1999 by Merck Research Laboratories, pp. 1417-1424.*

(Continued)

*Primary Examiner* — Eric S Olson
(74) *Attorney, Agent, or Firm* — Baker Botts L.L.P.

(57) ABSTRACT

The present disclosure provides compositions and methods for treating, ameliorating, or relieving at least one symptom associated with loss of blood flow to the brain including, without limitation, ischemic stroke. Compositions of the disclosure may comprise a bile acid compound and a carbohydrate, wherein both materials remain in solution for all pH values of the solution within a selected range of pH values. Symptoms may include infarct volume, functional recovery, apoptosis, and/or eNOS expression.

14 Claims, 5 Drawing Sheets
(3 of 5 Drawing Sheet(s) Filed in Color)

FOREIGN PATENT DOCUMENTS

| | | |
|---|---|---|
| EP | 0086705 | 2/1983 |
| EP | 0086705 | 8/1983 |
| EP | 0312052 | 10/1988 |
| EP | 0 312 052 A1 | 4/1989 |
| EP | 0 599 282 A1 | 11/1993 |
| EP | 1255566 | 11/2002 |
| EP | 1255566 A2 | 11/2002 |
| FR | 2710267 | 3/1995 |
| JP | 55 022616 A | 2/1980 |
| JP | 61171421 | 2/1986 |
| JP | 62153220 | 7/1987 |
| JP | 63104925 | 5/1988 |
| JP | 63243031 | 10/1988 |
| JP | 60 24991 A | 2/1994 |
| JP | 6024991 A | 2/1994 |
| JP | 2001522360 | 11/2001 |
| WO | WO 99/61481 | 12/1999 |
| WO | 00/04875 A2 | 2/2000 |
| WO | 01/56547 A2 | 8/2001 |
| WO | WO 2004/012686 | 2/2004 |
| WO | 2004/043342 | 5/2004 |
| WO | 2004/043342 A2 | 5/2004 |
| WO | 2004/096123 | 11/2004 |
| WO | WO2004/096123 | * 11/2004 |
| WO | WO 2006/026555 A2 | 3/2006 |
| WO | 2006/050165 | 5/2006 |
| WO | WO 2006/057637 A1 | 6/2006 |

OTHER PUBLICATIONS

Falasca et al., "Tauroursodeoxycholate Reduces Ischemic Damage in Human Allografts: A Biochemical and Ultrastructural Study" Transplantation Proceedings (2000) vol. 32 pp. 49-50.*
"Dacarbazine", Aidsmap Treatment and Care, http://www.aidsmap.com/en/docs/9685F4D7-D57C-4F10-A41F-D5EDF7811B3A.asp , pp. 1, Feb. 6, 2006.
"Drug Information: Dacarbazine", Medline Plus, http://www.nlm.nih.gov/medlineplus/druginfo/medmaster/a682750.html , pp. 2, Apr. 1, 2003.
"Dacarbazine", NCI Terminology Browser, http://nciterms.nci.nih.gov/NCIBrowser/PrintableReport.jsp?dictionary=NCI_Thesaurus&code=C411 , pp. 3, Nov. 2005.
P.J. Neveu, "The Effects of Thiol Moiety of Levamisole on Both Cellular and Humoral Immunity During the Early Response to a Hapten-Carrier Complex" Clin. Exp. Immunol. vol. 32, pp. 419-422, 1978.
E. Nagy et al., "Imuthiol Inhibits the Etoposide-Induced Apoptosis in HL-60 Cells" Immunology Letters vol. 64, pp. 1-4, 1998.
"An Assessment of the In Vivo Biological Effects of Diethyldithiocarbamate (DTC) in HIV-Infected Patients", ClinicalTrials.gov, http://www.clinicaltrials.gov/ct/show/NCT00000650;jsessionid=AF8903A542A345FA86641E2A559AC8C9?order=1, pp. 6, Feb. 27, 2006.
Hubner et al., "Enhancement of Monocyte Antimycobacterial Activity by Diethyldithiocarbamate (DTC)" Int. J. Immunopharmac. vol. 13, pp. 1067-1072, 1991.
"Diethyldithiocarbamate", http://nciterms.nci.nih.gov/NCIBrowser/ConceptReports.jsp? , pp. 2, Feb. 6, 2006.
"Proventil", PDR Health, http://www.pdrhealth.com/drug_info/rxdrugprofiles/drugs/pro1360.shtml, pp. 5, Feb. 8, 2006.
"Powered by Dorland's Illustrated Medical Dictionary: E", MerckSource, http://www.mercksource.com/pp/us/cns/cns_hl_dorlands.jspzQzpgzEzzSzp-pdocszSzuszSzcommonzSzdorlandszSzdorlandzSzdmd_e_17zPzhtm, pp. 3, Feb. 27, 2006.
F.S. Giorgi et al., "The role of norepinephrine in epilepsy: from the bench to the bedside" Neurosci. Behavioral. Rev.. vol. 28, pp. 507-524, 2004.
K. Bodin et al., "Antiepileptic drugs increase plasma levels of 4beta-hydroxycholesterol in humans: evidence for involvement of cytochrome p450 3A4" J. Biol. Chem. vol. 276, pp. 38685-38689, Oct. 19, 2001.
V.S. Kasture et al.,"Anticonvulsant activity of Albizzia lebbeck leaves" Indian Journal of Experimental Biology vol. 34, pp. 78-80, Jan. 1996.

V. Fontes et al., "Recurrent Aphthous Stomatitis: Treatment With Colchicine. An Open Trial of 54 Cases", Ann. Dermatol. Venereol. vol. 129, pp. 1365-1369 , (with abstract), 2002.
P.P. But et al., "Ethnopharmacology of bear gall bladder: I" Journal of Ethnopharmacology vol. 47, pp. 27-31, 1995.
K.G. Rajesh et al., "Hydrophilic Bile Salt Ursodeoxycholic Acid Protects Myocardium Against Reperfusion Injury in a P13K/Akt Dependent Pathway", Journal of Molecular and Cellular Cardiology, vol. 39, pp. 766-776, 2005.
Cecilia M.P. Rodrigues et al., "Ursodeoxycholic Acid May Inhibit Deoxycholic Acid-Induced Apoptosis by Modulating MitoChondrial Transmembrane Potential and Reactive Oxygen Species Production", Molecular Medicine, vol. 4, pp. 165-178, 1998.
"Drug Information: Hydralazine", Medline Plus, http://www.nlm.nih.gov/medlineplus/druginfo/medmaster/a682246.html, pp. 3, Apr. 1, 2003.
"Drug Information: Isoxsuprine (Systemic)", Medline Plus, http://www.nlm.nih.gov/medlineplus/druginfo/uspdi/202310.html , pp. 4, Jul. 15, 1994.
"Drug Information: Nylidrin (Systemic)", Medline Plus, http://www.nlm.nih.gov/medlineplus/druginfo/uspdi/202416.html , pp. 3, May 14, 1993.
"Drug Information: Dyphylline (Systemic)", Medline Plus, http://www.nlm.nih.gov/medlineplus/druginfo/uspdi/202752.html , pp. 4, Jun. 14, 1999.
"Drug Information: Bronchodilators, Andrenergic (Inhalation)", Medline Plus, http://www.nlm.nih.gov/medlineplus/druginfo/uspdi/202095.html , pp. 12, Jun. 25, 2003.
"Colfosceril Palmitate", Tiscali, http://www.tiscall.co.uk/lifestyle/healthfitness/health_advice/netdoctor/archive/100003422.html , pp. 2, 1998-2004.
"Selenium", PDR Health, http://www.pdrhealth.com/drug_info/nmdrugprofiles/nutsupdrugs/sel_0232.shtml, pp. 8, Feb. 27, 2006.
"Clean, Beautiful, Healthy Life", LG Household & Health Care, http://www.lgcare.com/english/aboutus/06.html, pp. 3, Feb. 27, 2006.
"Zovirax", PDRhealth, hhttp://www.pdrhealth.com/drug_info/rxdrugprofiles/drugs/zov1505.shtml , pp. 4, Feb. 8, 2006.
"Denavir", PDRhealth, http://www.pdrhealth.com/drug_info/rxdrugprofiles/drugs/den1123.shtml , pp. 2, Feb. 8, 2006.
V.S. Kasture et al.,"Anticonvulsive activity of Albizzia lebbeck, Hibiscus rosa sinesis and Butea monosperma in experimental animals" Journal of Ethnopharmacology vol. 71, pp. 65-75, 2000.
"Drug Information: Celecoxib", Medline Plus, http://www.nlm.nih.gov/medlineplus/druginfo/medmaster/a699022.html , pp. 4, Jan. 1, 2006.
R.L. Wynn, "New Reports on Dental Analgesics. NSAIDs and Cardiovascular Effects, Celecoxib for Dental Pain, and a New Analgesic—Tramadol with Acetaminophen" General Dentistry vol. 50, pp. 218-220, 222, May 2002.
R.L. Wynn, "Update on Nonprescription Pain Relievers for Dental Pain", General Dentistry vol. 52, pp. 94-98, Mar. 2004.
P.M. Preshaw et al., "Self-medication for the control of dental pain: what are our patients taking?", Dent Update vol. 21, pp. 299-301, 304, Sep. 1994.
A.D. McNaught, "Nomenclature of Carbohydrates", Pure and Applied Chemistry, vol. 68, pp. 1919-2008, 1996.
D.L. Nelson, "Carbohydrates and Glycobiology", Lehninger Principles of Biochemistry,Fourth Edition, pp. 238-271, 2005.
H.R. Horton, "Carbohydrates", Principles of Biochemistry, Second edition, pp. 228-234, 1996.
Gerhard Schmid, "Preperation and Industrial Production of Cyclodextrins", Comprehensive Supramolecular Chemistry, vol. 3, pp. 41-56, 1996.
Frömming, "Cyclodextrins", Cyclodextrins in Pharmacy, Chapter 1, pp. 1-18, 1994.
Frömming, "Cyclodextrin Derivatives", Cyclodextrins in Pharmacy, Chapter 2, pp. 19-32, 1994.
Lehninger et al., "Carbohydrates and Glycobiology", Principles of Biochemistry, pp. 301-307, 2000.
D.S. Alberts et al., "Phase III Trial of Ursodeoxycholic Acid to Prevent Colorectal Adenoma Recurrence", Journal of National Cancer Institute, vol. 97, No. 11, pp. 846-853, Jun. 1, 2005.

D. Gaist et al.; "Statins and Risk of Polyneuropathy"; Neurology, vol. 58; pp. 1333-1337, May 2002.

D. Chapman-Shimshoni et al.; "Simvastatin Induces Apoptosis of B-CLL cells by Activation of Mitochondrial Caspase 9"; Experimental Hematology, vol. 31; pp. 779-783, 2003.

C.J. Newton et al.; "Fluvastin Induces Apoptosis of Vascular Endothelial Cells: Blockade by Glucocorticoids"; Cardiovascular Surgery, vol. 11, No. 1; pp. 52-60, 2003.

M.A. Vandelli et al.; "2-Hydroxypropyl-β-Cyclodextrin Complexation With Ursodeoxycholic Acid"; International Journal of Pharmaceutics, vol. 118; pp. 77-83, 1995.

J.F. Dasta et al.; "Comparison of Visual and Turbidimetric Methods for Determining Short-Term Compatibility of Intravenous Critical-Care Drugs"; American Journal of Hospital Pharmacy; vol. 45; pp. 2361-2366, Nov. 1988.

C.A. Ventura et al.; "Improvement of Water Solubility and Dissolution Rate of Ursodeoxycholic Acid and Chenodeoxycholic Acid by Complexation With Natural and Modified β-Cyclodextrins"; International Journal of Pharmaceutics; vol. 149; pp. 1-13, 1997.

M. Föcking et al; "Statins Potentiate Caspase-3 Activity in Immortalized Murine Neurons"; Neuroscience Letters; vol. 355; pp. 41-44, 2003.

Michael B. Jacobs; "HMG-CoA Reductase Inhibitor Therapy and Peripheral Neuropathy"; www.PubMed.com ; pp. 3, Jun. 1, 1994.

Chad Silverberg; "Atorvastatin-Induced Polyneuropathy"; www.PubMed.com ; pp. 5, Nov. 4, 2003.

A.C. Peltier et al.; "Recent Advances in Drug-Induced Neuropathies"; Current Opinion in Neurology, vol. 15; pp. 633-638, 2002.

Park et al.; "Cisplatin-Induced Apoptotic Cell Death in Mouse Hybrid Neurons Is Blocked by Antioxidants Through Suppression of Cisplatin-Mediated Accumulation of p53 but Not of Fas/Fas Ligand"; Journal of Neurochemistry, vol. 75, No. 3; pp. 946-953, 2000.

R. Panini et al.; "Improvement of Ursodeoxycholic Acid Bioavailability by 2-Hydroxypropyl-β-Cyclodextrin Complexation in Healthy Volunteers"; Pharmacological Research; vol. 31, No. 314; pp. 205-209, 1995.

Invernizzi et al.; "Difference in the Metabolism and Disposition of Ursodeoxycholic Acid and of its Taurine-Conjugated Species in Patients with Primary Biliary Cirrhosis"; Hepatology, vol. 29, No. 2; pp. 320-327, 1999.

Itoh et al.; "Antibacterial action of bile acids against *Helicobacteria pylori* and changes inits ultrastructural morphology: effect of unconjugated dihydroxy bile acid"; J. Gastroenterol, vol. 34, pp. 571-576, 1999.

Knopp et al.; "Long-Term Blood Cholesterol-Lowering Effects of a Dietary Fiber Supplement", Am J Pre. Med (1999) 17(1):18-23.

F. Lanzarotto et al.; "Effect of Long-Term Simvastatin Administration as an Adjunct to Ursodeoxycholic Acid: Evidence for a Synergistic Effect on Biliary Bile Acid Composition but Not on Serum Lipids in Humans", GUT, (1999) vol. 4 pp. 552-556.

Leuschner et al., "Oral Budesonide and Ursodeoxycholic Acid for Treatment of Primary Billary Cirrhosis: Results of a Prospective Double-Blind Trial", Gastroenterology, (1999) vol. 117 pp. 918-925.

Na et al., "Cloud Point of Nonionic Surfactants: Modulation with Pharmaceutical Excipients", Pharmaceutical Research, (1999) vol. 16, No. 4 pp. 562-568.

Osato et al., "Osmotic Effect of Honey on Growth and Viability of *Helicobacter pylori* ", Digestive Diseases and Sciences, (1999) vol. 44, No. 3 pp. 462-464.

Sinisalo et al., "Ursodeoxycholic Acid and Endothelial-Dependent, Nitric Oxide-Independent Vasodilatation of Forearm Resistance Arteries in Patients with Coronary Heart Disease", Br. J. Clin. Pharamcol., (1999) vol. 47 pp. 661-665.

Verrips et al., "Effect of Simvastatin in Addition to Chenodeoxycholic Acid in Patients with Cerebrotendinous Xanthomatosis", Metabolism, (1999) vol. 48, No. 2 pp. 233-238.

Wacker Biochem. Corp., advertisement, *C&EN*, 31 (Apr. 12, 1999).

M. A. Hammad, B. W. Müller, Increasing Drug Solubility by Means of Bile Salt-Phosphatidylcholine-Based Mixed Micelles, European J. of Pharmaceutics and Biopharmaceutics. (1998) vol. 46 pp. 361-367.

M. A. Hammad et al., "Solubility and Stability of Tetrazepam in Mixed Micelles", European J. of Pharmaceutical Sciences, (1998) vol. 7 pp. 49-55.

Oliva et al., "Ursodeoxycholate Alleviates Alcoholic Fatty Liver Damage in Rats", Alcohol Clin Exp Res., (1998), vol. 22, No. 7,pp. 1538-1543.

Rodrigues et a;l, "Ursodeoxycholic Acid May Inhibit Deoxyxholic Acid-Induced Apoptosis by Modulating Mitochondrial Transmembrane Potential and Reactive Oxygen Species Production", Molecular Medicine (1998) 4: 165-178.

Invernizzi et al., "Ursodeoxycholate inhibits induction of NOS in human intestinal epithelial cells and in vivo", Am J Physiol (1997) 273:G131-138.

Keith D. Lindor, M.D., "Ursodiol for Primary Sclerosing Cholangitis", The New England Journal of Medicine, (1997) vol. 336, No. 10., pp. 691-695.

Binek et al., "Bedeutung von Ursodeoxycholsäure bei der Eradikation von *Helicobacter pylori*", Schweitz Med Wochenschr (1996) 126 (Suppl. 79): 44S-46S.

Crosignani, et al., "Clinical Pharamcokinetics of Therapeutic Bile Acids", Clin. Pharmacokinet, (1996) vol. 30, No. 5 pp. 333-358.

Han et al., "The Interaction of pH, Bile and *Helicobacter pylori* May Explain Duofenial Ulcer", American Journal of Gastroenterology (1996) vol. 91, No. 6, pp. 1135-1137.

Mohler et al., "Effect of Ursodeoxycholic Acid on HCV Replication in Subtyped Chronic Hepatitis C", Digestive Diseases and Sciences, (1996) vol. 41, No. 6 p. 1276.

Newman et al., "Starch", Analytical Profiles of Drug Substances, (1996) Bristol-Myer Squibb Pharmaceutical Research Institute, New Brunswick, NJ, pp. 523-577.

Nishigaki, et al., "Ursodeoxycholic Acid Corrects Defective Natural Killer Activity by Inhibiting Prostaglandin $E_2$ Production in Primary Biliary Cirrhosis", Digestive Diseases and Sciences, (1996) vol. 41, No. 7, pp. 1487-1493.

Panini et al., "The Influence of 2-Hydroxypropyl-β-Cyclodextrin on the Haemolysis Induced by Bile Acids", J. Pharm. Pharmacol., (1996) vol. 48 pp. 641-644.

Tanaka et al., "Ligand-Independent Activiation of the Glucocorticord Receptor by Ursodeoxycholic Acid", The Journal of Immunology (1996) 156:1601-1608.

Buckley et al., "Controlled Release Drugs in Overdose Clinical Consideration", Drug Safety (1996) vol. 12, No. 1 pp. 73-84.

Jorgensen et al., "Characterisation of patients with a complete biochemical response to ursodeoxycholic acid", GUT (1995) 36:935-938.

Klumra et al., "A 1-h Topical Therapy for the Treatment of *Helicobacter pylori* Infection", Am. J. Gastercenterol. (1995) vol. 90, No. 1, pp. 60-63.

Lindor et al., "The Combination of Ursodeoxycholic Acid and Methotrexate for Patients with Primary Biliary Cirrhosis: The Results of a Pilot Study", Hepatology (1995) vol. 22, No. 4 pp. 1158-1162.

Rodrigues et al., "The Site-Specific Delivery of Ursodeoxycholic Acid to the Rat Colon by Sulfate Conjugation", Gastroenterology (1995) vol. 109 pp. 1835-1844.

Simoni et al., "Bioavailability Study of a New, Sinking, Enteric-Coated Ursodeoxycholic Acid Formulation", Pharmacological Research (1995) vol. 31, No. 2 pp. 115-119.

P.J. Sinko, "Utility of Pharmacodynamic Measures for Assessing the Oral Bioavailability of Peptides. 1. Administration of Recombinant Salmon Calcitonin in Rats", Journal of Pharmaceutical Sciences, (1995) vol. 84, No. 11, pp. 1374-1378.

A. Benjamin Suttle and Kim L. R. Brouwer, "Regional Gastronintestinal Absorption of Ranitidine in the Rat", Pharmaceutical Research, (1995) vol. 12, No. 9 pp. 1311-1315.

"Pharmaceutical Necessities", Remington: The Science and Practice of Pharmacy, Mack Printing Co., Easton, Pennsylvania (1995) pp. 1409-1410.

Angelin et al., "Effects of Ursodeoxycholic Acid on Plasma Lipids", Scand J. Gastroenterol. (1994) 29 Suppl 204:24-26.

I. Björkhem, "Inborn Errors of Metabolism with Consequences for Bile Acid Biosynthesis: A Minireview", Scand J. Gastroenteral (1994) 29 Suppl. 204:68-72.

A. Björkland and T.H. Totterman, "Is Primary Biliary Cirrhosis an Autoimmune Disease?", Scand J. Gastroenteral (1994) 29 Suppl. 204:32-9.

Boberg et al., "Etiology and Pathogenesis in Primary Sclerosing Cholangitis", Scand J. Gastroenterol (1994) 29 Suppl. 204:47-58.

Cirillo N.W. and F.R. Zwas., "Ursodeoxycholic Acid in the Treatment of Chronic Liver Disease", Am J Gastroenterol (1994) vol. 89, No. 9 pp. 1447-1452.

K. Einarsson, "Effect of Urodeoxycholic Acid on Hepatic Cholesterol Metabolism", Scand J. Gastroenteral (1994) 29 Suppl. 204:19-23.

S. Friman and J Svarik, "A Possible Role of Ursodeoxycholic Acid in Liver Transplantation", Scand J. Gastroenteral (1994) 29 Suppl. 204:62-4.

A.F. Hofmann, "Pharmacology of Ursodeoxycholic Acid, an Enterohepatic Drug", Scand J. Gastroenteral (1994) 29 Suppl. 204:1-15.

U. Leuschner et al., "Ursodeoxycholic Acid Therapy in Primary Biliary Cirrhosis", Scand J. Gastroenteral (1994) 29 Suppl. 204:40-6.

Lindor et al., "Ursodeoxycholic Acid in the Treatment of Primary Biliary Cirrhosis", Gastroenteral (1994) 106:1284-1290.

McLeod et al., "Glucocorticoid-Dextran Conjugates as Potential Prodrugs for Colon-Specific Delivery: Hydrolysis in Rat Gastrointestinal Tract Contents", J. Pharm Sci., (1994) vol. 83, No. 9., pp. 1284-1288.

McLeod et al., "Glucocorticoid-Dextran Conjugates as Potential Prodrugs for Colon-Specific Delivery: Steady-State Pharamacokinetics in the Rat", Biopharmaceutics & Drug Disposition, (1994) vol. 15, pp. 151-161.

Paumgartner et al., "Ursodeoxycholic Acid Treatment of Cholesterol Gallstone Disease", Scand J. Gastroenterol (1994) 29 Suppl 204: 28-31.

Poupon, et al., "Ursodiol for the Long-Term Treatment of Primary Billary Cirrhosis", The New England Journal of Medicine, (1994) vol. 330, No. 19, pp. 1342-1347.

Roda et al., "Improved Intestinal Absorption of an Enteric-Coated Sodium Ursodeoxycholate Formulation", Pharmaceutical Research, (1994) vol. 11, No. 5 pp. 642-647.

Roda et al., "Influence of Ursodeoxycholic Acid on Biliary Lipids", Scand J Gastroenterol (1994) 29 Suppl. 204:16-8

A. Stiehl, "Ursodeoxycholic Acid Therapy in Treatment of Primary Sclerosing Cholangitis", Scand J Gastroenterol (1994) 29 Suppl. 204:59-61.

Strandvik et al., "Cystic Fibrosis: Is Treatment with Ursodeoxycholic Acid of Value?", Scand J Gastroenterol (1994) 29 Suppl. 204:65-7.

McLeod et al., "Synthesis and Chemical Stability of Glucocoritcoid-Dextran Esters: Potential Prodrugs for Colon-Specific Delivery", International J. of Pharmaceutics, (1993) vol. 92 pp. 105-114.

Gerrit H. P. Te Wierik et al., "Preparation, Characterization, and Pharmaceutical Application of Linear Dextrins, I. Preparation and Characterization of Amylodextrin, Metastable Amylodextrins, and Metastable Amylose", Pharmaceutical Research, (1993) vol. 10, No. 9 pp. 1274-1279.

Gerritt H. P. Te Wierik et al., "Preparation, Characterization, and Pharmaceutical Application of Linear Dextrins. II. Complexation and Dispersion of Drugs with Amylodextrin by Freeze-Drying and Kneading", Pharmaceutical Research, vol. 10, No. 9 pp. 1280-1284, 1993.

G. H. P. Te Wierik et al., "Preparation, Characterization and Pharmaceutical Application of Linear Dextrins: IV. Drug Release from Capsules and Tablets Containing Amylodextrin", International J. of Pharmaceutics, (1993) vol. 98 pp. 219-224.

Scott L. Myers et al., "Solid-State Emulsions: The Effects of Maltodextrin on Microcrystalline Aging", Pharmaceutical Research, (1993) vol. 10, No. 9 pp. 1389-1391.

Dressman et al., "Gastrointestinal Parameters that Influence Oral Medications", J. of Pharmaceutical Sciences, (1993) vol. 82, No. 9 pp. 857-872.

Thorsteinn Loftsson et al., "The Effect of Cyclodextrins on the Solubility and Stability of Medroxyprogesterone Acetate and Megestrol Acetate in Aqueous Solution", International J. of Pharmaceutics, (1993) vol. 98 pp. 225-230.

Beuers et al., "Ursodeoxycholic Acid for Treatment of Primary Sclerosing Cholangitis: A Placebo-controlled Trial", Hepatology. (1992) vol. 16, No. 3, pp. 707-714.

Bode et al., "Polymorphism in *Helicobacter pylori*—a key function in recurrence of infection", Medizinische Klinik, , (1992) 87(4):179-84.

Colombo et al., "Ursodeoxycholic Acid Therapy in Cystic Fibrosis-associated Liver Disease: A Dose-response Study", Hepatology, (1992) vol. 16, No. 4 pp. 924-930.

De Caprio et al., "Bile Acid and sterol solubilization in 2-hydroxypropyl-Ǝ-cyclodextrin", Journal of Lipid Research, (1992) vol. 33, pp. 441-443.

Fried et al., "Ursodeoxycholic Acid Treatment of Refractory Chronic Graft-versus-Host Disease of the Liver", Annals of Internal Medicine, (1992) 116:624-629.

Walker et al., "Intestinal Absorpotion of Ursodeoxycholic Acid in Patients With Extrahepatic Biliary Obstruction and Bile Drainage", Gastroenterology (1992) 102:810-815

M.L. Hanninen, "Sensitivity of *Helicobacter pylori* to Different Bile Salts", Eur. J. Clin. Microbiol. Infect., (1991) vol. 10, pp. 515-518.

Mathai et al., "The effect of bile acids on the growth and adherence of *Helicobacter pylori*", Aliment Pharmacol Therap. (1991) 5, pp. 653-668.

Rolandi et al., "Effects of ursodeoxycholic acid (UDCA) on serum liver damage indices in patients with chronic active hepatitis", Eur J. Clin Pharmacol (1991) 40:473-476.

Tan et al., "Studies on Complexation between β-Cyclodextrin and Bile Salts", International J. Pharmaceutics, (1991) vol. 74 pp. 127-135.

G. Buck, "*Campylobacter pylori* and Gastrroduodenal Disease". Clinical Microbiology Reviews, (1990) vol. 3, No. 1 pp. 1-12.

Chazouilleres et al., "Ursodeoycholic Acid for Primary Sclerosing Cholangitis", J. Hepatology, (1990) vol. 11 pp. 120-123.

Colombo et al., "Effects of Ursodeoxycholic Acid Therapy for Liver Disease Associated with Cystic Fibrosis", J. of Pediatrics, (1990) vol. 117, No. 3 pp. 482-489.

M. Y. Morgan, "Branched Chain Amino Acids in the Management of Chronic Liver Disease Facts and Fantasies", J. of Hepatology, (1990) vol. 11 pp. 133-141.

Podda et al., "Effect of Different Doses of Ursofeoxycholic Acid in Chronic Liver Disease", Digestive Diseases and Sciences, (1989) vol. 34, No. 12, Suppl. pp. 59S-65S.

Aigner A and Bauer A, "Bile acids, Long known active substances with a future", Med Monatsschr Pharm (1988) (11): 369-75.

Dioguardi et al., "The role of oral branched-chain amino acids (BCAAs) in the elevation of plasma ammonia (pNH$_3$)", Chapter 68, in Advances in Ammonia Metabolism and Hepatic Encephalopathy, Soeters et al., eds., (1988) Elsevier Science Publishers B.V., pp. 527-533.

Montanari et al., "Oral administration of branched-chain amino acids (BCAAs) in liver cirrhosis (LC): effect on their intra- and extracellular pools", Chapter 67, in Advances in Ammonia Metabolism and Hepatic Encephalopathy, Soeters et al., eds., (1988) Elsevier Science Publishers B.V., pp. 519-526.

N.F.H. Ho, "Utilizing Bile Acid Carrier Mechanisms to Enhance Liver an Small Intestine Absorption", Annals New York Academy of Sciences, (1987) 507:315-29.

Fiaccadori et al., "The effect of dietary supplementation with branchchain amino acids (BCAAs) vs. casein in patients with chronic recurrent portal systemic encephalopathy: a controlled trial", pp. 489-497. (1988) Elsevier Science Publishers B.V. Advances in ammonia metabolism and hepatic encephalopathy.

D.S. Tompkins and AP West. "Campylobacterpylori, acid and bile", J. Clin. Pathol. (1987) 40:1387.

Van Caekenberghe et al., "In Vitro Synergistic Activity between Bismuth Subcitrate and Various Antimicrobial Agents against *Campylobacter pylorids*", Antimicrobial Agent and Chemotherapy, (1987) vol. 31, No. 9, pp. 1429-1430.

Miyajima et al., "Interaction of β-Cyclodextrin with Bile Salts in Aqueos Solutions", Chem. Pharm. Bull., (1986) vol. 34, No. 3 pp. 1395-1398.

Golub et al., "Physiologic Considerations in Drug Absorption from the Gastrointestinal Tract", J. Allergy Clin. Immunol., (1986) vol. 78, No. 4, Part 2 pp. 689-694.
Gordon et al., "Nasal Absorption of Insulin: Enhancement by Hydrophobic Bile Salts", Proc. Natl. Acad. Sci., (1985) vol. 82 pp. 7419-7423.
Parquet et al., "Bioavailability, Gastrointestinal Transit, Solubilization and Faecal Excretion of Ursodeoxycholic Acid in Man", European J. of Clinical Investigation, (1985) vol. 15 pp. 171-178.
Stefaniwsky et al., "Ursodeoxycholic Acid Treatment of Bile Reflux Gastritis", Gastroenterology (1985)vol. 89, pp. 1000-1004.
K. Müller, "Structural Aspects of Bile Salt-Lecithin Mixed Micelles", Hepatology, (1984) vol. 4, No. 5 pp. 134S-137S.
Murakami et al., "Effect of Bile Salts on the Rectal Absorption of Sodium Ampicillin in Rats", Chem. Pharm. Bull., (1984) vol. 32, No. 5 pp. 1948-1955.
Zentler-Munro et al., "Effect of Intrajejunal Acidity on Aqueous Phase Bile Acid and Lipid Concentrations in Pancreatic Steatorrhoea Due to Cystic Fibrosis", Gut (1984) vol. 25 pp. 500-507.
Moses et al., "Insulin Administered Intranasally as an Insulin-Bile Salt Aerosol Effectiveness and Reproducibility in Normal and Diabetic Subjects", Diabetes, (1983) vol. 32 pp. 1040-1047.
Ziv et al., "Bile Salts Facilitate the Absorption of Heparin from the Intestine", Biochemical Pharmacology, (1983) vol. 32, No. 5 pp. 773-776.
Armstrong et al., "The Hydrophobic-Hydrophilic Balance of Bile Salts. Inverse Correlation between Reverse-Phase High Performance Liquid Chromatographic Mobilities and Micellar Cholesterol-Solubilizing Capacities", J. Lipid Research, (1982) vol. 23 pp. 70-80.
Podda et al., "Gallstone Dissolution After 6 Months of Ursodeoxycholic Acid (UDCA): Effectiveness of Different Doses", J. Int. Med. Res., (1982) vol. 10 pp. 59-63.
Hirai et al., "Effect of Surfactants on the Nasal Absorption of Insulin in Rats", International J. of Pharmaceutics, (1981) vol. 9 pp. 165-172.
Hirai et al., "Mechanisms for the Enhancement of the Nasal Absorption of Insulin by Surfactants", International J. Phamaceutics, (1981) vol. 9 pp. 173-184.
Hollander et al., "Intestinal Absorption of Aspirin, Influence of pH, Taurocholate, Ascorbate and Ethanol", J. Lab. Clin. Med., (1981) vol. 98, No. 4 pp. 591-595.
Reynier et al., "Comparative Effects of Cholic, Chenodeoxycholic, and Ursodeoxycholic Acids on Micellar Solubilization and Intestinal Absorption of Cholesterol", J. Lipid Research, (1981) vol. 22 pp. 467-473.
Igimi et al., "pH-Solubility Relations of Chenodeoxycholic and Ursodeoxycholic Acids: Physical-Chemical Basis for Dissimilar Solution and Membrane Phenomena", J. Lipid Research, (1980) vol. 21 pp. 72-90.
Carey et al., "Micelle Formation by Bile Salts", Arch Intern Med, (1972) vol. 130, pp. 506-527.
Database WPI Section Ch, Week 198824 Derwent Publications Ltd., London, GB, AN-1988-165730 XP002337363 & JP 63104925 A, 1988.
Database WPI Section Ch, Week 198846 Derwent Publications Ltd., London, GB, AN-1988-327783 XP002337364 & JP 63243031 A, 1988.
European Office Action for Application No. 04 812 094.3, 8, Applicant: Seo Hong Yoo, 8 pages, Dec. 17, 2007.
CN Office Action; Application No. 200580028815.X; pp. 10, Mar. 13, 2009.
Isreali Office Action; Application No. 181434; pp. 12, Mar. 22, 2009.
CN Office Action; Application No. 200480044467.0; pp. 7 Mar. 27, 2009.
CN Office Action; Application No. 200580034884.1; pp. 6, Mar. 27, 2009.
Hofmann et al.; "Bile Acid Solubility and Preperation in Vitro and in Vivo: The Role of Conjugation, pH, and Ca2+ Ions"; Journal of Lipid Research, vol. 33; pp. 617-626, 1992.
Kimura et al.; "A Case of Cerebrotendinous Xanthomatosis: Effects of Ursodeoxycholic Acid Administration on Serum Bile Acids and Cholestanol"; Jap J Med, vol. 21, No. 3; pp. 210-215, Jul. 1982.

Ribatti et al.; "Development of the Blood-Brain Barrier: A Historical Point of View"; The Anotomical Record (Part B: New Anat.); pp. 6, 2006.
Ota et al.; "Metabolism of Bile Acids IV*. Absorption, Distribution, Excretion, and Metabolism of Orally Administered Ursodeoxycholic Acid in Rats"; Hiroshima Journal of Medical Sciences, vol. 26, No. 4; pp. 233-251, Dec. 1977.
MacWalter et al.; "A Benefit-Risk Assessment of Agents Used in the Secondary Prevention of Stroke"; Drug Safety; vol. 25, No. 13; pp. 943-963, 2002.
Wardlaw et al.; "Thrombolysis for Acute Ischaemic Stroke"; Cochrane Database of Systematic Views; Issue 3; pp. 98, 2003.
International Preliminary Report on Patentability; PCT/US2006/036325; pp. 8, Mar. 26, 2009.
Chinese Office Action; Application No. 200580037307.8; pp. 6, May 15, 2009.
European Office Action; Application No. 05 792 858.2-2123; pp. 4, May 20, 2009.
C.M.P. Rodrigues et al.; "Neuroprotection by a Bile Acid in an Acute Stroke Model in the Rat"; Journal of Cerebral Blood Flow & Metabolism, vol. 22; pp. 463-471, 2002.
Isreal Office Action; Application No. 181434; pp. 1, Sep. 7, 2009.
European Office Action; Application No. 05 813 305.9-1216; pp. 16, Jan. 19, 2010.
Kathleen Parfitt: "Martindale: The Complete drug reference, 32nd edition", Pharmaceutical Press, London, UK, pp. 629-630 (Zalcitabine), Jan. 1, 1999.
Kathleen Parfitt: "Martindale: The Complete drug reference, 32nd edition", Pharmaceutical Press, London, UK, pp. 607-609 (Didanosine), Jan. 1, 1999.
Kathleen Parfitt: "Martindale: The Complete drug reference, 32nd edition", Pharmaceutical Press, London, UK, pp. 556-558 (Paclitaxel), Jan. 1, 1999.
Kathleen Parfitt: "Martindale: The Complete drug reference, 32nd edition", Pharmaceutical Press, London, UK, pp. 513-515 (Cisplatin), Jan. 1, 1999.
Kathleen Parfitt: "Martindale: The Complete drug reference, 32nd edition", Pharmaceutical Press, London, UK, pp. 593 (Sumarin), Jan. 1, 1999.
Mitsuyoshi H et al.; "Ursodeoxycholic acid protects hepatocytes against oxidative injury via induction of antioxidants"; Biochemical and Biophysical Research Communications, vol. 263, No. 2; pp. 537-542, ISSN: 0006-291X, Sep. 24, 1999.
Sun Ah Park et al.; "Cisplatin-induced apoptotic cell death in mouse hybrid neurons is blocked by antioxidants through suppression of cisplatin-mediated accumulation of p53 but not of Fas/Fas ligand"; Journal of Neurochemistry, vol. 75, No. 3; pp. 946-953; ISSN: 0022-3042, 2000.
Isreal Office Action; Application No. 182805; pp. 2, Oct. 15, 2009.
"Dacarbazine", NCI Terminology Browser, http://nciterms.nci.nih.gov/NCIBrowser/PrintableReport.jsp?dictionary=NCI_Thesaurus&code=C411 , pp. 3, Feb. 7, 2006.
Communication pursuant to Article 94(3) EPC; Application No. 05 813 305.9-1216; pp. 7, Mar. 7, 2008.
Dominguez et al. "Low in Vivo Toxicity of a Novel Cisplatin-Ursodeoxycholic Derivative (Bamet-UD2) with Enhanced Cytostatic Activity versus Liver Tumors" Journal of Pharmacology and Experimental Therapeutics, vol. 297, No. 3 (pp. 1106-1112), 2000.
Tudca; "Neuroprotective Effect of Taurourosodeoxycholic Acid (TUDCA) in Motor Neuronal Cells Expressing Mutated Cu/Zn Superoxide Dismutase (SOD1)"; Seoul National University Library; pp. 39, 2002.
Australian Examination Report; Application No. 2005279961; pp. 2, Mar. 5, 2010.
Chinese Office Action and Translation; Application No. 20050028815; pp. 19, Mar. 11, 2010.
Russian Office Action with English translation; Application No. 2007106563/14(007118); Pgs., Jan. 25, 2010.
Australian Examination Report; Appliaction No. 2005302452; pp. 2, May 6, 2010.
Israeli Office Action and translation; Israeli Patent Application No. 181434; pp. 4, Sep. 5, 2010.

Russian Office Action and English translation; Russian Patent Application No. 2007106563; pp. 12, Sep. 27, 2010.
Extended European Search Report; Application No. 1017611.2-2123; pp. 7, Oct. 25, 2010.
Japanese Office Action (w/translation); Application No. 2000-560868; pp. 10, Oct. 9, 2009.
Office Action from related Chinese Application dated Mar. 28, 2011.
Rodrigues et al. "Neuroprotection by a Bile Acid in an Acute Stroke Model in the Rat" Journal of Cerebral Blood Flow & Metabolism, vol. 22 (pp. 463-471), 2002.
Ma et al. "Ursodeoxycholic acid inhibits endothelin-1 production in human vascular endothelial cells" European Journal of Pharmacology, vol. 505 (pp. 67-74), 2004.
Chu et al. "Human neural stem cells improve sensorimotor deficits in the adult rat brain with experimental focal ischemia" Brain Research 1016 (pp. 145-153), 2004.
International Preliminary Report on Patentability and Written Opinion for International Application No. PCT/US2005/030679 (9 pages), Mar. 6, 2007.
H.P.R. Bootsma et al.; "β-Cyclocextrin as an Excipient in Solid Oral Dosage Forms: in Vitro and in Vivo Evaluation of Spray-Dried Diazepam-β-Cyclodextrin Products"; Inernation Journal of Pharmaceutics, vol. 51; pp. 213-223, 1989.
M.C. Allwood et al.; "Stability of Ampicillin Infusions in Unbuffered Saline"; International Journal of Pharmaceutics, vol. 97; pp. 219-224, 1993.
Higginbottom et al., International Journal of Pharmaceutics, vol. 109, pp. 173-180, 1994.
Kirk et al; "Inclusion Compounds"; Encyclopedia of Chemical Technology, Fourth Edition; vol. 14 pp. 125-135, 1995.
PCT International Search Report and Written Opinion, PCT/US2004/039507, 29 pages, Mailing Date Oct. 25, 2005.
International Preliminary Report on Patentability and Written Opinion for International Application No. PCT/US2004/039507 (21 pages), Jun. 7, 2007.
Thao et al., "Antibacterial and anti-atrophic effects of a highly soluble, acid stable UDCA formula in Helicobacter pylori-induced gastritis"; Biochemical Pharmacology; BCP-9750; pp. 12, 2008.
XP 002337365, Jul. 8, 1987, XP (abstract).
XP 002337364, Oct. 7, 1988, XP (abstract).
XP 002337367, Feb. 1, 1994, XP (abstract).
Mollan, Jr. et al. "On of Aqueous Soluble Starch Conversion Products" Maltodextrin (pp. 308-349), 1995.
"Maltrin Maltodextrins & Corn Syrup Solids Chemical and Physical Properties" GPC Technical Bulletin, TB31-021296, Grain Processing Corp. (Brochure +4 pages), 1999.
Hirai et al. "Mechanisms for the Enhancement of the Nasal Absorption of Insulin by Surfactants" International J. of Pharmaceutics, vol. 9 (pp. 173-184), 1981.
PCT International Search Report PCT/US2004/039507 (12 pages), Mailing Date May 8, 2005.
International Search Report and Written Opinion for International Application No. PCT/US2006/036325 (13 pages), Jun. 4, 2007.
XP 002337363, May 10, 1998, XP (abstract).
Carey, MD et al. "Micelle Formation by Bile Salts Physical-Chemical and Thermodynamic Considerations" Arch. Intern. Med., vol. 130 (pp. 506-527), Oct. 1972.
Hollander et al. "Intestinal Absorption of Aspirin Influence of pH, Taurocholate, Ascorbate and Ethanol" J. of Lab. Clin. Med., vol. 98, No. 4 (pp. 591-595), Oct. 1980.
Igimi et al. "ph-Solubility Relations of Chenodeoxycholic and Ursodeoxycholic Acids: Physical-Chemical Basis for Dissimilar Solution and Membrane Phenomena" J. of Lipid Research, vol. 21 (pp. 72-90), 1980.
Reynier et al. "Comparative Effects of Cholic, Chenodeoxycholic, and Ursodeoxycholic Acids on Micellar Solubilization and Intestinal Absorption of Cholesterol" J. of Lipid Research, vol. 22 (pp. 467-473), 1981.
Nagamatsu "Phase I Clinical Study of Ursodesoxycholic Acid" Jpn. Pharmacol. Ther. vol. 22, No. 6 (pp. 145-159), 1997.
Notification Concerning Transmittal of International Preliminary Report on Patentability; PCT/US2006/008925; pp. 6, Apr. 16, 2008.

The American Heritage Dictionary, Second College Edition, Houghton Mifflin Company, pp. 1213, 1982.
Cannon et al. "Reduction of pain on intravenous infusion with bile salt formulations for a macrolide antibiotic" International Journal of Pharmaceutics, vol. 114, No. 1 (pp. 65-74), Jul. 13, 1994.
Villaneuva et al. "Effect of Bile Acids of Hepatobiliary Transport of Cisplatin by Perfused Rat Liver" Pharmacology and Toxicology, vol. 80, No. 3 (pp. 111-117), Sep. 26, 1996.
Remington: The Science and Practice of Pharmacy, Lippincott Williams and Wilkins, pp. 218, 2000.
Takeda et al., "Prevention of Irinotecan (CPT-11)-Induced Darrhea by Oral Alkalization Combined with Control of Defecation in Cancer Patients" International Journal of Cancer, vol. 92, pp. 269-275, 2001.
Schuldes et al., " Reversal of Multidrug Resistance and Increase in Plasma Membrane Fluidity in CHO Cells with R-Verapamil and Bile Salts", European Journal of Cancer vol. 37, pp. 660-667, 2001.
Dominguez et al. "Low in Vivo Toxicity of a Novel Cisplatin-Ursodeoxycholic Derivative (Bamet-UD2) with Enhanced Cytostatic Activity versus Liver Tumors" Journal of Pharmacology and Experimental Therapeutics, vol. 297, No. 3 (pp. 1106-1112), Jan. 16, 2001.
PCT Notification of Transmittal of the International Search Report and Written Opinion PCT/US2006/008925, 10 pages, Mailing Date Jul. 21, 2006.
Chemical Abstracts Registry Entry 191595-91-2, "Bamet R2" American Chemical Society, Copyright 2007.
Chemical Abstracts Registry Entry 64480-66-6, "Glycoursodeoxycholic Acid", American Chemical Society, Copyright 2007.
International Search Report and Written Opinion for International Application No. PCT/US2005/037211 (16 pages), Feb. 13, 2007.
International Preliminary Report on Patentability for International Application No. PCT/US2005/037211 (10 pages), Apr. 26, 2007.
Y. Hattori, et al.; "Ursodeoxycholic Acid Inhibits the Induction of Nitric Oxide Synthase"; European Journal of Pharmacology; pp. 147-150, 1996.
G.D. Ghadge et al.; "Mutant Superoxide Dismutase-1-Linked Familial Amyotrophic Lateral Sclerosis: Molecular Mechanisms of Neuronal Death and Protection"; The Journal of Neuroscience, vol. 17, No. 22; pp. 8756-8766, Nov. 15, 1997.
C.M.P. Rodrigues et al.; "Bilirubin and Amyloid-β Peptide Induce Cytochrome c Release Through Mitochondrial Membrane Permeabilization"; Molecular Medicine, vol. 6, No. 11; pp. 936-946, 2000.
C.D. Keene et al.; "A Bile Acid Protects Against Motor and Cognitive Deficits and Reduces Striatal Degeneration in the 3-Nitropropionic Acid Model of Huntington's Disease"; Experimental Neurology, vol. 171; pp. 351-360, 2001.
C.M.P. Rodrigues et al.; "The Therapeutic Effects of Ursodeoxycholic Acid as an Anti-Apoptotic Agent"; Expert Opin. Investig. Drugs, vol. 10, No. 7; pp. 1243-1253, 2001.
D. Lapenna et al.; "Antioxidant Properties of Ursodeoxycholic Acid", Biochemical Pharmacology, vol. 64; pp. 1661-1667, 2002.
Drug Name: Tauroursodeoxycholic Acid (TUDCA), TUDCA-Various/UDCA (Ursodiol-Actigall, Watson Pharmacceuticals, Novartis, Generics), 7 pages, 2004.
E. Diguet et al.; "Effects of Riluzole on Combined MPTP + 3-Nitropropionic Acid-Induced Mild to Moderate Striatonigral Degeneration in Mice"; Journal of Neural Transmission; pp. 19, 2004.
L. Dupuis et al.; "Evidence for Defective Energy Homeostasis in Amyotrophic Lateral Sclerosis: Benefit of a High-Energy Diet in a Transgenic Mouse Model"; www.pnas.org/cgi/doi/10.1073/pnas.0402026101 ; PNAS, Jul. 27, 2004, vol. 101, No. 30, pp. 11159-11164, Jul. 27, 2004.
International Search Report and Written Opinion; PCT/US2005/039089; pp. 15, Mailed: May 24, 2006.
EMEA/CHMP/EWP Workshop; "Slowing the Progression of Neurodegenerative Diseases: Medicinal Productions (MP) Clinical Development"; European Medicines Agency, Pre-authorisation Evaluation of Medicines for Human Use; http://www.emea.europa.eu; pp. 15, Oct. 2, 2006.

Chemical Abstracts Registry Entry 265093-50-3, "Barnet UD2", American Chemical Society, Copyright 2007.

27th Annual Meeting of the Korean Neurological Association; "Oral Presentation"; Journal of the Korean Neurological Association; vol. 26, Suppl. 2; pp. 3, 2008.

Chinese Office Action for Patent Application 01804549.9, 6 pages, Oct. 30, 2008.

Brazilian Office Action for Patent Application PI 9912395-9, 6 pages, Dec. 5, 2008.

Deborah F. Gelinas; "Riluzole"; ALS and Other Motor Neuron Disorders,(Suppl 4); pp. 3-4, 2000.

N. Shibata et al.; "Molecular Biological Approaches to Neurological Disorders Including Knockout and Transgenic Mouse Models"; Neuropathology, vol. 22; pp. 337-349, 2002.

R.E. Castro et al.; "The Bile Acid Tauroursodeoxycholic Acid Modulates Phosphorylation and Translocation of Bad via Phosphatidylinositol 3-Kinase in Glutamate-Induced Apoptosis of Rat Cortical Neurons"; American Society for Pharmacology and Experimental Therapeutics; pp. 34, Jun. 9, 2004.

International Preliminary Report on Patentability for International Application No. PCT/US2005/039089 (9 pages), May 10, 2007.

European Office Action for Application No. 05 820 886.9, 3 pages, Nov. 14, 2008.

Indian First Examination Report; Application No. 1990/KOLNP/2007; pp. 58, Dec. 14, 2010.

Japanese Office Action with English Translation; Japanese Patent Application No. 2007-530237; pp. 12 (Oct. 7, 2011).

* cited by examiner

NEUROPROTECTIVE EFFECT OF SOLUBILIZED UDCA IN FOCAL ISCHEMIC MODEL

RELATED APPLICATION

This application claims priority to U.S. provisional patent application No. 60/605,566, filed on Aug. 30, 2004 and U.S. provisional patent application No. 60/629,998, filed on Nov. 22, 2004, both of which are hereby incorporated in their entirety by reference.

TECHNICAL FIELD

The present disclosure relates to a system and process for providing clear aqueous solutions of one or more bile acids that may reduce stroke.

BACKGROUND

According to recent U.S. statistics, it is estimated that over 400,000 patients have a first-time stroke each year. In addition, stroke may be the leading cause of disability and the third leading cause of death. Men may be at a higher risk of having a stroke than women. About 80% of all strokes may be acute ischemic strokes (due to, e.g., intracranial thrombosis or extracranial embolism). About one quarter of all strokes occur in individuals under 65 years old, a figure which is somewhat at odds with a perception that stroke is a disease of the elderly.

An ischemic cascade may be initiated in the first seconds to minutes following the loss of perfusion to the brain. Absent therapeutic intervention, neurological damage results. This damage may be divided into two regions, an infarction area in which damage may be irreversible and an ischemic penumbra in which damage may be reversible. However, in the hours and days following loss of circulation, damage in the penumbra, like that in the infarct, becomes irreversible.

SUMMARY

Therefore, a need exists for therapies that reduce the infarction volume and/or preserve neurological function. Accordingly, the present disclosure relates to bile acid compositions that may reduce infarction volume and/or enhance functional recovery after ischemic stroke. In some embodiments, without being limited to any particular mechanism of action, this may occur through inhibition of apoptosis and/or enhancement of eNOS expression. In one aspect, the present disclosure provides compositions which comprise (1) a bile acid, a bile acid derivative, a bile acid salt, or a bile acid conjugated with an amine, (2) water, and (3) a sufficient quantity of an aqueous soluble starch conversion product such that the bile acid and the starch conversion product remain in solution at any pH within a selected pH range.

The disclosure further relates to a composition which comprises (1) a bile acid, a bile acid derivative, a bile acid salt, or a bile acid conjugate with an amine, (2) water, and (3) a sufficient quantity of an aqueous soluble non-starch polysaccharide such that the bile acid and the polysaccharide remain in solution at any pH within a selected pH range.

The disclosure further relates to a pharmaceutical composition which comprises (1) a bile acid, a bile acid derivative, a bile acid salt, or a bile acid conjugate with an amine, (2) water, (3) a pharmaceutical compound in a pharmaceutically appropriate amount, and (4) a sufficient quantity of an aqueous soluble starch conversion product and an aqueous soluble non-starch polysaccharide such that the bile acid, the pharmaceutical compound, and the carbohydrate remain in solution at any pH level within a selected pH range. According to one non-limiting embodiment of the disclosure, the pharmaceutical compound may be anti-stroke therapeutic molecule or mixture.

The disclosure further relates to solution dosage forms of bile acid compositions. These solution dosage forms may display improved bioavailability and/or absorbability and/or membrane permeability of a bile acid. These solution dosage forms may also display improved bioavailability and/or absorbability and/or membrane permeability of a pharmaceutical compound. In addition, the presence of bile acid may reduce or eliminate toxicity and/or side effect(s) of a pharmaceutical.

In some embodiments of the disclosure, a composition is provided which comprises (1) a bile acid, a bile acid derivative, a bile acid salt, or a bile acid conjugated with an amine, (2) water, and (3) a sufficient quantity of carbohydrate such that the bile acid component and the carbohydrate remain in solution at any pH within a selected pH range, wherein the carbohydrate is a combination of an aqueous soluble starch conversion product and an aqueous soluble non-starch polysaccharide. In embodiments containing both soluble non-starch polysaccharide and high molecular weight starch conversion product, the amounts of each are such that when combined together in the composition they are sufficient to allow a bile acid component, a high molecular weight starch conversion product, a soluble non-starch polysaccharide and a pharmaceutical compound, if any, to remain in solution at any pH within a selected pH range.

In some embodiments of the disclosure, a combination therapy composition is provided which may increase the intensity of response to or efficacy of a pharmaceutical. Such a composition may permit administration of lower dosages of a pharmaceutical compound, attack a disease complex at different points, affect elimination and/or alter absorption of a pharmaceutical compound. Compositions of the disclosure may, in some embodiments, lead to or contribute to a reduction in toxicity and/or side effects of a pharmaceutical.

In some embodiments, the present disclosure relates to methods of reducing infarction volume of an ischemic stroke in a subject having or at risk of having an ischemic stroke. Such methods may include administering to the subject a composition comprising (a) a bile acid material selected from the group consisting of a bile acid, an aqueous soluble derivative of a bile acid, a bile acid salt, and a bile acid conjugated with an amine by an amide linkage; (b) a carbohydrate selected from the group consisting of an aqueous soluble starch conversion product or an aqueous soluble non-starch polysaccharide; and (c) water, wherein the bile acid material and the carbohydrate both remain in solution for all pH values of the solution within a selected range of pH values and wherein infarction volume is reduced.

The present disclosure, in some embodiments, relates to methods of enhancing functional recovery in a subject having or at risk of having an ischemic stroke. According to some embodiments, functional recovery may include, without limitation, any restoration of any neurological, cognitive, sensory, and/or motor function. Such methods may include administering to the subject a composition comprising (a) a bile acid material selected from the group consisting of a bile acid, an aqueous soluble derivative of a bile acid, a bile acid salt, and a bile acid conjugated with an amine by an amide linkage; (b) a carbohydrate selected from the group consisting of an aqueous soluble starch conversion product or an aqueous soluble non-starch polysaccharide; and (c) water, wherein the bile acid material and the carbohydrate both remain in solution for all pH values of the solution within a selected range of pH values and wherein functional recovery is improved.

According to some embodiments, the disclosure relates to methods of reducing infarction volume of increasing the expression of eNOS in a subject having or at risk of having an ischemic stroke. Such methods may include administering to the subject a composition comprising (a) a bile acid material selected from the group consisting of a bile acid, an aqueous soluble derivative of a bile acid, a bile acid salt, and a bile acid conjugated with an amine by an amide linkage; (b) a carbohydrate selected from the group consisting of an aqueous soluble starch conversion product or an aqueous soluble non-starch polysaccharide; and (c) water, wherein the bile acid material and the carbohydrate both remain in solution for all pH values of the solution within a selected range of pH values and wherein eNOS expression is increased.

In some embodiments, the present disclosure relates to methods of enhancing functional inhibiting apoptosis and increasing the expression of eNOS in a subject having or at risk of having an ischemic stroke. Such methods may include administering to the subject a composition comprising (a) a bile acid material selected from the group consisting of a bile acid, an aqueous soluble derivative of a bile acid, a bile acid salt, and a bile acid conjugated with an amine by an amide linkage; (b) a carbohydrate selected from the group consisting of an aqueous soluble starch conversion product or an aqueous soluble non-starch polysaccharide; and (c) water, wherein the bile acid material and the carbohydrate both remain in solution for all pH values of the solution within a selected range of pH values and wherein apoptosis is reduced and eNOS expression is increased.

The present disclosure, in some embodiments, relates to methods of treating ischemic stroke (e.g., treating, ameliorating, or relieving at least one symptom associated with ischemic stroke) in a subject having or at risk of having an ischemic stroke. Such methods may include administering to the subject a composition comprising (a) a bile acid material selected from the group consisting of a bile acid, an aqueous soluble derivative of a bile acid, a bile acid salt, and a bile acid conjugated with an amine by an amide linkage; (b) a carbohydrate selected from the group consisting of an aqueous soluble starch conversion product or an aqueous soluble non-starch polysaccharide; and (c) water, wherein the bile acid material and the carbohydrate both remain in solution for all pH values of the solution within a selected range of pH values and wherein the ischemic stroke (e.g., at least one symptom of the ischemic stroke) is treated.

According to some embodiments, the disclosure relates to methods of delivering a bile acid material to the brain (e.g., across the blood brain barrier) in a subject. Such methods may include administering to the subject a composition comprising (a) a bile acid material selected from the group consisting of a bile acid, an aqueous soluble derivative of a bile acid, a bile acid salt, and a bile acid conjugated with an amine by an amide linkage; (b) a carbohydrate selected from the group consisting of an aqueous soluble starch conversion product or an aqueous soluble non-starch polysaccharide; and (c) water, wherein the bile acid material and the carbohydrate both remain in solution for all pH values of the solution within a selected range of pH values and wherein a bile acid material is delivered to the brain.

BRIEF DESCRIPTION OF THE DRAWINGS

The patent application file contains at least one drawing executed in color. Copies of this patent or patent application publication with color drawing(s) will be provided by the United States Patent and Trademark Office upon request and payment of the necessary fee.

Some specific example embodiments of the disclosure may be understood by referring, in part, to the following description and the accompanying drawings, wherein.

DETAILED DESCRIPTION

Figure 1B:
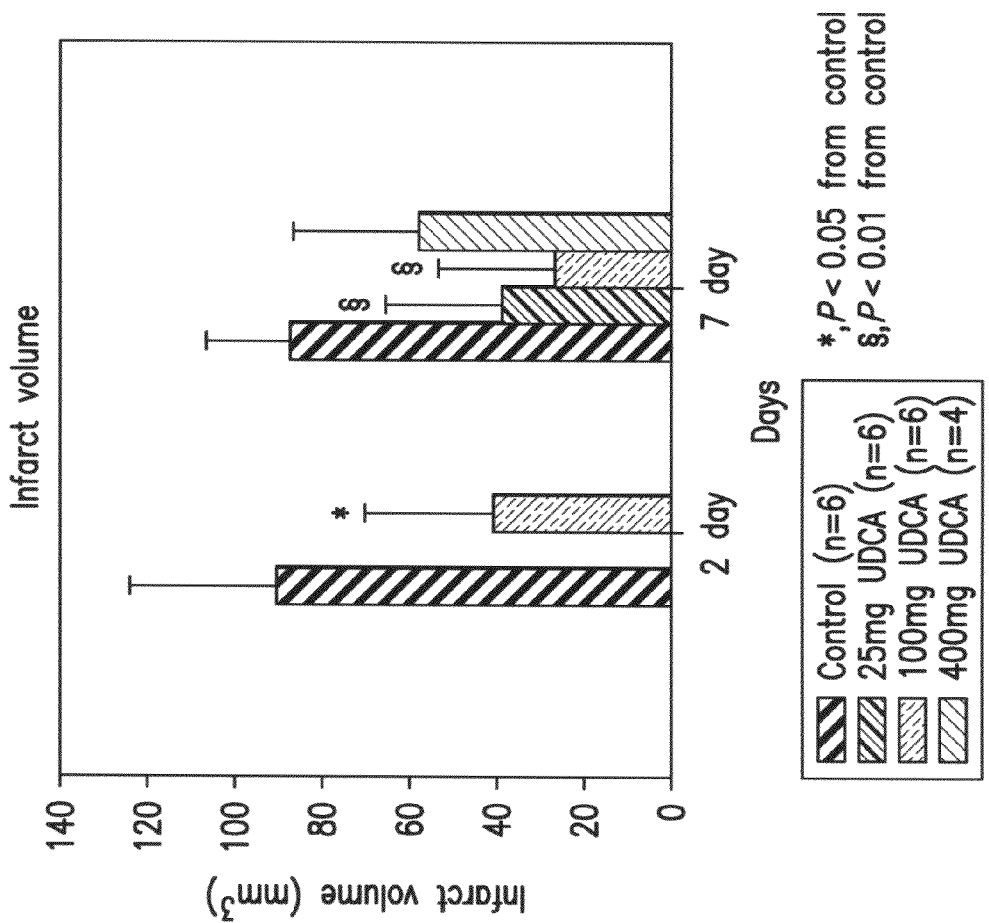
FIG. 1B shows a graphical representation of infarct volume 2 and 7 days after reperfusion (data are presented as mean±SD (n=6 respectively)

Ursodeoxycholic acid (3α-7β-dihydroxy-5β-cholanic acid) ("UDCA"), a major component of bear bile, and other forms of bile acid are highly hydrophobic. Many are insoluble in aqueous solution at physiological and acidic pH (e.g., below about pH 8.4). In addition, while UDCA and other bile acids may be well tolerated when administered orally, they may have an acutely bitter and disagreeable taste and aftertaste.

Pharmacological actions of UDCA may include, without limitation, dose-dependent: (1) replacement and/or displacement of toxic bile acids, (2) cytoprotective effects, (3) stabilization and/or protection of cell membranes, (4) antiapoptotic effects, (5) immunomodulatory effects (e.g., due to activation of the intracellular glucocorticoid receptor), (6) antiinflammatory effects (e.g., due to repression of NF-kB and inhibition of the induction of nitric oxide synthase), (7) stimulation of bile secretion, and (8) stimulation of exocytosis and insertion of canalicular membrane transporters.

Some forms of bile acid may be useful as a therapeutic agent for one or more conditions. For example, UDCA may be useful for the treatment of one or more conditions including, without limitation, protection against many types of liver disease. Its medicinal uses may include dissolution of radiolucent gall stones and one or more cholestatic disorders including, without limitation, primary biliary cirrhosis, primary sclerosing cholangitis, intrahepatic cholestasis of pregnancy, cystic fibrosis-associated liver disease, a pediatric liver disorder, and chronic graft-versus-host disease of the liver.

In spite of these useful pharmacological properties of bile acids as therapeutically active agents and as carriers and/or adjuvants, commercial use of bile acids may be limited by poor solubility and/or bioavailability. For example, many bile acid formulations include a solid from of bile acid either as a component of a tablet or as a particle and/or precipitate in a solution or suspension. These formulations may contain crystals of bile acid, which are poorly soluble at pH 1 to 8. Dissolution of crystal UDCA may be extremely slow and incomplete.

In some cases, less than from about 30% to about 60% of administered UDCA may be absorbed. This may occur principally in the small intestine by dissolution-limited passive nonionic diffusion. Improved solubilization for UDCA crystals may be possible at an endoluminal pH over about 8.4, but this value has been unobtainable in vivo during either pancreatic or duodenal secretion. Accordingly, many existing forms of bile acid have scant bioavailability. This, in turn, means that the levels of bile in systemic circulation following administration of many existing forms of UDCA may be extremely low. Therefore, many existing bile acid formulations have limited utility for delivering UDCA systemically and even less utility for delivering UDCA to the brain.

Hepatocytes may take up and conjugate UDCA and then excrete it in bile in a process called first-pass clearance. The concentration of UDCA in bile may reach a peak from about 1 hour to about 3 hours following administration. Free UDCA in bile may be reabsorbed by cholangiocytes. This phenomenon, called the cholehepatic shunt, may be linked to increased biliary bicarbonate secretion. The degree of UDCA enrichment in biliary bile following chronic ingestion may correlate with its daily-administered dose. Using some existing UDCA formulations, doses above 10±12 mg/kg per day may not further increase the proportion of UDCA in bile. This may be due to its epimerization to chenodeoxycholic acid and/or an inability to inhibit hepatic synthesis of primary bile acids. Therefore, the absorption of UDCA may actually decrease with increasing doses of UDCA using existing formulations. Accordingly, a need exists for bile compositions with increased solubility, bioavailability, and/or membrane permeability. In addition, a need exists for bile compositions that undergo less epimerization of UDCA to CDCA.

According to some embodiments of the present disclosure, salts, precursors, and/or derivatives of ursodeoxycholic acid (UDCA) may have a beneficial effect on subjects who experience an interruption in the supply of blood to brain tissue. Therapeutic delivery of bile acids to brain may be hindered by enterohepatic circulatory action of UDCA, extremely low concentration of UDCA in the blood, and reduced membrane permeability due to strong hydrophilicity and acidic character. Embodiments of the present disclosure provide bile formulations that may ameliorate or overcome these hindrances.

According to specific example embodiments of the present disclosure, the neuroprotective effect of a solubilized bile acid formulation was tested. Sixty three transient focal ischemic rats were prepared by transient focal ischemic model. Solubilized UDCA was intravenously administered once at various doses immediately after reperfusion in five groups; saline only, 25 mg UDCA/kg, 100 mg UDCA/kg, 400 mg UDCA/kg, and 400 mg TUDCA/kg respectively. In each group, the infarct volume and functional outcome were measured, and brains were obtained for bile acid analysis. Infarct volume decreased and behavioral scores improved in rats treated with solubilized UDCA. Decreased TUNEL-positive cells within the penumbra, lower caspase activity, and a high cerebral concentration of UDCA was observed in the solubilized UDCA treated group. Accordingly, but without being limited to any particular mechanism of action, solubilized UDCA may have a neuroprotective effect against cerebral ischemia by an antiapoptotic mechanism and/or an antiinflammatory action.

In some embodiments, soluble bile acids may include, without limitation, any type of aqueous soluble bile acids. A bile acid salt may be, in some embodiments, any aqueous soluble salt of a bile acid. According to some embodiments, aqueous dissolved salts of bile acids may be formed by the reaction of bile acids described above and an amine including but not limited to aliphatic free amines such as trientine, diethylene triamine, tetraethylene pentamine, and basic amino acids such as arginine, lysine, ornithine, and ammonia, and amino sugars such as D-glucamine, N-alkylglucamines, and quaternary ammonium derivatives such as choline, heterocyclic amines such as piperazine, N-alkylpiperazine, piperidine, N-alkylpiperidine, morpholine, N-alkylmorphline, pyrrolidine, triethanolamine, and trimethanolamine. According to some specific example embodiments of the disclosure, aqueous soluble metal salts of bile acids, inclusion compound between the bile acid and cyclodextrin and its derivatives, and aqueous soluble O-sulfonated bile acids may also be included as soluble bile acid salts.

Soluble bile acid derivatives of this disclosure may be those derivatives which are as soluble as or more soluble in aqueous solution than is the corresponding underivatized bile acid. Bile acid derivatives include, but are not limited to derivatives formed at the hydroxyl and carboxylic acid groups of the bile acid with other functional groups including but not limited to halogens and amino groups. Soluble bile acid may include an aqueous preparation of a free acid form of bile acid combined with a mineral acid (e.g., hydrochloric acid, sulphuric acid, phosphoric acid, and acidic phosphate) and/or an organic acid (e.g., citric acid, tartaric acid, and acetic acid).

According to some embodiments, bile acids may include, without limitation, ursodeoxycholic acid, chenodeoxycholic acid, cholic acid, hyodeoxycholic acid, deoxycholic acid, 7-oxolithocholic acid, lithocholic acid, iododeoxycholic acid, iocholic acid, tauroursodeoxycholic acid, taurochenodeoxycholic acid, taurodeoxycholic acid, taurolithocholic acid, glycoursodeoxycholic acid, taurocholic acid, glycocholic acid, and their derivatives at a hydroxyl or carboxylic acid group on the steroid nucleus. In some embodiments, however, a composition of the disclosure may exclude one or more of the foregoing bile acids (e.g., tauroursodeoxycholic acid).

In some embodiments of the disclosure, delivery of bile acid (e.g., UDCA) in solution may achieve higher in vivo levels of bile acid (e.g., UDCA) than existing preparations. Therefore, the therapeutic potential of bile acid (e.g., UDCA) may be more fully achieved than existing formulations. Since bile acid may be completely dissolved in the formulations of the disclosure, higher in vivo levels of bile acid may be achieved in some embodiments, even though lower doses are administered.

According to some embodiments, compositions of the disclosure may be administered to a subject through any effective mode including, without limitation, The hormone may be administered through any effective mode including, without limitation, through any orifice and/or through skin. For example, routes of administration may include oral administration, sublingual administration, parenteral administration, intradermal injection, subcutaneous injection, intrathyroid injection, intravenous injection, intranasal administration, transdermal administration, and transconjunctival administration.

In some embodiments, compositions of the disclosure may have a form selected from the group consisting of ingestible tablet, buccal tablet, troches, capsule, elixir, suspension, syrup, wafer, pill, granule, powder, cachet, emulsion, liquid, aerosol, soft or hard gelatin capsule, sterilized liquid for injection, sterilized powder and the like.

In some embodiments of the disclosure, a plurality of bile acids may be used in a single formulation. Mixtures of two or more bile salts of differing hydrophobic activity may behave as a single bile salt of an intermediate hydrophobic activity. As a result, detergent properties and the toxicity of mixtures of two bile acids of differing hydrophobic activity may be intermediate between the individual components.

Carbohydrates suitable for use in the disclosure may include aqueous soluble starch conversion products and aqueous soluble non-starch polysaccharides. According to some embodiments of the present disclosure, aqueous soluble starch conversion products may include carbohydrates obtained directly from the partial or incomplete hydrolysis of starch under various pH conditions. Non-limiting examples may include maltodextrin, dextrin, liquid glucose, corn syrup solid (dried powder of liquid glucose), and soluble starch. In some embodiments, a carbohydrate may be selected from the group consisting of MALTRIN® M200, MALTRIN® M2050, a corn syrup solid, and MALTRIN® M700, MALTRIN® M040, MALTRIN® M050, MALTRIN® M100, MALTRIN® M150, MALTRIN® M180, a maltodextrin, both of which may be manufactured by GPC®, Grain Processing Corporation of Muscatine, Iowa. For the purpose of this embodiment, the term "corn syrup" may include both corn syrup and liquid glucose. If a starch conversion product is polymeric, the polymer may have at least one reducing end and at least one non-reducing end and may be linear or branched. The molecular weight may be from about 100 mass units to over 106 mass units.

According to some embodiments of the present disclosure, aqueous soluble non-starch polysaccharides may be obtained under various pH conditions by various hydrolytic or synthetic mechanisms. Non-limiting examples include to dextran, guar gum, pectin, indigestible soluble fiber. If polymeric, the polymer may have at least one reducing end and at least one non-reducing end. The polymer may be linear or branched. The molecular weight may be from about 100 mass units to over 106 mass units.

The amount of high molecular weight aqueous soluble starch conversion product and/or soluble non-starch polysaccharide used in embodiments of the disclosure is at least the amount needed to render the chosen bile acid(s) in the preparation soluble in the concentration desired and in the pH range desired. In some embodiments of the disclosure, the approximate minimal weight ratio of maltodextrin to UDCA required to prevent UDCA precipitation may be 6:1 (i.e. 1.2 g for every 0.2 g of UDCA, 6 g for every 1 g of UDCA, and 12 g for every 2 g of UDCA in 100 mL of water). In some embodiments of the disclosure, the approximate minimal quantity of maltodextrin may be 30 g for every 200 mg of chenodeoxycholic acid, 12 g for every 200 mg of 7-ketolithocholic acid, 10 g for every 200 mg of cholic acid and 50 g for every 200 mg of deoxycholic acid. In some embodiments of the disclosure, the approximate minimal weight ratio of liquid glucose (commercial light corn syrup) to UDCA required to prevent the precipitation of bile acids from the aqueous solution dosage forms of the disclosure may be about 160:1 (i.e. 80 g for every 500 mg UDCA in 100 mL water and 80 g for every 500 mg ursodeoxycholic acid in 200 mL water). The minimal required quantity of high molecular weight aqueous soluble starch conversion products or soluble non-starch polysaccharide may be determined primarily by the absolute quantity of bile acids in the solution formulation rather than the concentration.

In some embodiments of the disclosure, a formulation may comprise cyclodextrin in addition to a starch conversion product and/or a non-starch polysaccharide. In other embodiments, compositions of the disclosure exclude cyclodextrin and its derivatives.

In some embodiments of the disclosure, the formulation further comprises dietary fiber. Non-limiting examples of dietary fiber may include guar gum, pectin, psyllium, oat gum, soybean fiber, oat bran, corn bran, cellulose, and wheat bran.

In some embodiments of the disclosure, the formulation may further comprise an emulsifying agent. In some embodiments of the disclosure, an emulsifying agent may include emulsifying agents and suspending agents. Non-limiting examples of emulsifying agents may include guar gum, pectin, acacia, carrageenan, carboxymethyl cellulose sodium, hydroxymethyl cellulose, hydroxypropyl cellulose, methyl cellulose, polyvinyl alcohol, povidone, tragacanth gum, xanthan gum, and sorbitan ester.

The selected pH range for which the formulation will not precipitate its bile acid, starch conversion product, soluble non-starch polysaccharide, and/or its pharmaceutical compound may be any range of pH levels obtainable with an aqueous system. For example, this range may be between about pH 1 and about pH 14 or between about pH 1 and about pH 10. In some embodiments, the range may be any subset of the range of pH levels obtainable in an aqueous system sufficient for a pharmaceutical formulation to remain in solution. For example, a pharmaceutical may remain in solution from preparation, to administration, to absorption in the body, according to the method of administration. Thus, the composition may be used as a pharmaceutical formulation wherein the pharmaceutical compound remains in solution without precipitation at prevailing pH levels in the mouth, stomach and intestines. In some embodiments of the disclosure, a bile acid remains dissolved under acidic conditions as a free bile acid in spite of the general insolubility of bile acids under acidic conditions.

A pharmaceutical compound may affect the response to another drug (e.g., quantitatively or qualitatively). For example, a quantitative effect may occur where co-administration with bile acid increases the intensity of the therapeutic effect of the pharmaceutical compound. A qualitative effect may occur, for example, where co-administration with bile acid leads to production of different or additional active moieties in vivo.

According to the disclosure, the use of a broad range of pharmaceuticals is contemplated. Non-limiting examples include hormones, hormone antagonists, analgesic, antipyretics, anti-inflammatory drugs, immunoactive drugs, antineoplastic drugs, antibiotics, anti-inflammatory agents, sympathomimetic drugs, anti-infective drugs, anti-tumor agents, and anesthetics. Further non-limiting examples include drugs that target or affect the gastrointestinal tract, liver, cardiovascular system, and respiratory system. Further non-limiting examples of pharmaceutical compounds include insulin, heparin, calcitonin, ampicillin, octreotide, sildenafil citrate, calcitriol, dihydrotachysterol, apomorphine, yohimbine, trazadone, acyclovir, amantadine.HCl, rimantadine.HCl, cidofovir, delavirdine.mesylate, didanosine, famciclovir, foscarmet sodium, fluorouracil, ganciclovir sodium, idoxuridine, interferon-α, lamivudine, nevirapine, penciclovir, ribavirin, stavudine, trifluridine, valacyclovir.HCl, zalcitabine, zidovudine, indinavir.$H_2SO_4$, ritonavir, nelfinavir.$CH_3SO_3H$, saquinavir.$CH_3SO_3H$, d-penicillamine, chloroquine, hydroxychloroquine, aurothioglucose, gold sodium thiomalate, auranofin levamisole, dacarbazine, isoprinosine, methyl inosine monophosphate, muramyl dipeptide, diazoxide, hydralazineHCl, minoxidil, dipyridamole, isoxsuprine.HCl, niacin, nylidrin.HCl, phentolamine, doxazosin.$CH_3SO_3H$, prazosin.HCl, terazocin.HCl, clonidine-HCl, nifedipine, molsidomine, amiodarone, acetylsalicylic acid, verapamil, diltiazem, nisoldipine, isradipine, bepridil, isosorbide.dinitrate, pentaerythrytol.tetranitrate, nitroglycerin, cimetidine, famotidine, nizatidine, ranitidine, lansoprazole, omeprazole, misoprostol, sucralfate, metoclopramide.HCl, erythromycin, bismuth compound, alprostadil, albuterol, pirbuterol, terbutaline.$H_2SO_4$, salmetrol, aminophylline, dyphylline, ephedrine, ethylnorepinephrine, isoetharine, isoproterenol, metaproterenol, nedocromil, oxtriphylline, theophylline, bitolterol, fenoterol, budesonide, flunisolide, beclomethasone.dipropionate, fluticasone.propionate, codeine, codeine sulfate, codeine phosphate, dextromethorphan-HBr, triamcinolone-acetonide, montelukast sodium, zafirlukast, zileuton, cromolyn sodium, ipratropium bromide, nedocromil sodium benzonate, diphenhydramine.HCl, hydrocodone.bitartarate, methadone.HCl, morphine sulfate, acetylcysteine, guaifenesin, ammonium carbonate, ammonium chloride, antimony potassium tartarate, glycerin, terpinehydrate, colfosceril palmitate, atorvastatin.calcium, cervastatin.sodium, fluvastatin.sodium, lovastatin, pravastatin.sodium, simvastatin, picrorrhazia kurroa, andrographis paniculata, moringa oleifera, albizzia lebeck, adhatoda vasica, curcuma longa, momordica charantia, gymnema sylvestre, terminalia arjuna, azadirachta indica, tinosporia cordifolia, metronidazole, amphotericin B, clotrimazole, fluconazole, haloprogin, ketoconazole, griseofulvin, itraconazole, terbinafin.HCl, econazole.$HNO_3$, miconazole, nystatin, oxiconazole.$HNO_3$, sulconazole-$HNO_3$, cetirizine.2HCl, dexamethasone, hydrocortisone, prednisolone, cortisone, catechin and its derivatives, glycyrrhizin, glycyrrhizic acid, betamethasone, fludrocortisone.acetate, flunisolide, fluticasone.propionate, methyl prednisolone, somatostatin, lispro, glucagon, proinsulin, insoluble insulins, acarbose, chlorpropamide, glipizide, glyburide, metformin.HCl, repaglinide, tolbutamide, amino acid, colchicine, sulfinpyrazone, allopurinol, piroxicam, tolmetin sodium, indomethacin, ibuprofen, diflunisal, mefenamic acid, naproxen, and trientine.

Additional examples of pharmaceutical compounds that may be included in a composition of the disclosure may include, without limitation, any compound that becomes or remains soluble when added to a formulation of the disclosure, any compound that enhances the efficacy of another agent (e.g., by amplifying the desirable response, lowering dose needed to achieve same level of effect, diversifying the mechanism(s) of action, or improving absorption), and any compound that reduces the toxicity of an agent (e.g., administered at the same time and/or another time). According to some embodiments in which a composition of the disclosure includes an additional pharmaceutical compound, a bile acid in solution may act as an adjuvant, carrier, or enhancer. For example, a bile acid may enhance a therapeutic effect or metabolism of the additional pharmaceutical compound.

In some embodiments, a therapeutically active agent may include, without limitation, an anticoagulant (e.g., anisindion, dicumarol, warfarin sodium, citrate dextrose solution, danaproid sodium, heparin sodium), a fibrinolytic inhibitor (e.g., aminocaproic acid, tranexamic acid), an antiplatelet compound (e.g., ticlopidine HCl, clopidogrel bisulfate, eptifibatide, tirofiban HCL), a calcium channel blocker (e.g., amlodipine salts, bepridil HCL, diltiazem HCL, felodipine, Nifedipine), a corticosteroid (e.g., betamethasone, dexamethasone, fludrocortisone, flunisolide, hydrocortisone), a ganglionic blocking agent (e.g., mecamylamine HCl, trimethaphan camsylate), a hemopoietic growth factor (e.g., erythropoietin, granulocyte colony stimulating factors), a hemostatic compound (e.g., microfibrillar collagen, absorbable gelatin, thrombin), a nitric oxide donor (e.g., L-arginine, nitric oxide synthase inhibitors), a thrombolytic agent (e.g., amciximab, alteplase, streptokinase, urokinase), a vasoactive agent (e.g., diazoxide, hydralazine HCl, minoxidil), an oriental medicine (e.g., dan shen, dengzhanhua, didang tang), and Individual compounds (e.g., ginkgo biloba, lubeluzole, mannitol solution, naftidrofury, pentoxifylline, propentofylline, pentifylline piracetam, prostacyclin, puerarin, sanchi, theophylline, aminophylline, tirilazad, triflusal, vinpocetin).

Some embodiments of the disclosure may be practiced with pH adjustable agents. Non-limiting examples include HCl, phosphoric acid, $H_2SO_4$, $HNO_3$, $CH_3COOH$, citric acid, malic acid, tartaric acid, lactic acid, eidetic acid, phosphate and alkalies.

In some embodiments of the disclosure, the formulation is modified such that it may be administered as a liquid, solid, powder or tablet. In some embodiments of the disclosure, the formulation is comprised in a syrup, thick syrup or paste. A non-limiting example of a syrup is a solution of maltodextrin wherein the concentration of maltodextrin is less than 1.0 kg/L. A non-limiting example of a thick syrup is a solution of maltodextrin wherein the concentration of maltodextrin is between 1.0 kg/L and 1.2 kg/L inclusive. A non-limiting example of a paste is a solution of maltodextrin wherein the concentration of maltodextrin is greater than 1.2 kg/L.

Compositions of the present disclosure may, in some embodiments, be administered in conjunction with other stroke therapy including, without limitation, supportive care, treatment of neurological complications, antithrombotic therapy, thrombolytic therapy, and recombinant tissue-type plasminogen activator (rt-PA) therapy.

According to some embodiments of the disclosure, an aqueous solution comprising a bile acid compound and a carbohydrate is clear (i.e., free of precipitate visible to the human eye). Clarity, according to some embodiments may be assessed by visual inspection and/or spectrophotometric methods (Dasta J F et al., Am. J. Hospital Pharm. (1988) 45:2361-2366). According to embodiments in which spectrophotometric methods are used, absorbance may be detected at any useful wavelength including, without limitation, 260 nm, 400 nm, 580 nm, 680 nm, and 720 nm. In some embodiments, absorbance of a solution of the disclosure is compared with a water alone or water with the carbohydrate, but without the bile acid compound. The comparative difference at a selected wavelength, in some embodiments, may be less than 0.1 absorbance units, while in others it may be less than 0.05 absorbance units. In some embodiments, the difference may be less than 0.01 absorbance units or even less than 0.005 absorbance units.

In some embodiments, bile solutions of the disclosure may be dried ("dried s-UDCA"). A dried form may be derived from a solution formulations of bile acid compositions by lyophilization, evaporation, or any other means of dehydration known in the art. A solution of the disclosure may be partially dried to produce a semi-solid forms. The solutions may be thoroughly dried to form a solid, powder and granule. In some embodiments, a dried form may have less than about 20% of its original water content. In some embodiments, a dried form may have less than about 10% of its original water content. In some embodiments, a dried form may have less than about 5% of its original water content. In some embodiments, a dried form may have less than about 1% of its original water content. In some embodiments, a dried form may have less than about 0.2% of its original water content. In some embodiments, dried forms of the aqueous solutions may be substantially free of water. Dried forms may be dried by fluid process, tray process, spray process, and/or freezing process. Dried forms may be administered directly, as solid dosage forms or combined with water prior to administration.

In some embodiments, compositions of the disclosure may be prepared according to the methods disclosed in U.S. patent application Ser. No. 09/778,154 filed Feb. 5, 2001 and/or U.S. patent application Ser. No. 10/996,945 filed Nov. 24, 2004, both of which are hereby incorporated in their entirety by reference.

EXAMPLES

Example 1

Soluble UDCA Preparation

A clear aqueous solution of solubilized UDCA (s-UDCA) comprising an intact UDCA and an aqueous soluble starch which has low dextrose equivalency was prepared. Briefly, 6.48 g of sodium hydroxide pellets was dissolved in 500 mL of purified water. Next, 60 g of UDCA was dissolved in the sodium hydroxide solution with stirring at room temperature. Then, 400 g of carbohydrate (maltodextrin) was added portion by portion into the clear solution and was stirred. Into the resulting clear solution, sweetener, preservatives (and/or sweetener and flavoring agents) were added in quantities suitable for a pharmaceutical formulation. The pH of the clear solution was adjusted to 7-7.5 with sodium biphosphate. Purified water was added to make total 1000 mL. If desired, the clear solution may be filtered by stericup filter unit having 0.22 µm and GP plus membrane.

Example 2

Soluble UDCA Preparation

A clear aqueous solution of solubilized UDCA (s-UDCA) comprising an intact UDCA and an aqueous soluble starch which has low dextrose equivalency was prepared. Briefly, 1.1 g of sodium hydroxide pellets was dissolved in 500 mL of purified water. Next, 10 g of UDCA was dissolved in the sodium hydroxide solution with stirring at room temperature. Then, 500 g of carbohydrate (corn syrup solid) was added portion by portion into the clear solution and was stirred. Into the resulting clear solution, sweetener, preservatives (and/or sweetener and flavoring agents) were added in quantities suitable for a pharmaceutical formulation. The pH of the clear solution was adjusted to 7-7.5 with sodium biphosphate. Purified water was added to make total 1000 ml.

This composition had a Cmax of 20.4 µg/mL, which was 7 times higher than that reported for actigall produced by Novartis Pharmaceuticals, Newark, N.J. Data from "Results of a phase I multiple-dose clinical study of ursodeoxycholic Acid" Cancer Epidemiol Biomarkers Prev. 2004 May; 13(5): 861-7. In addition, this composition displayed a Tmax 5.5 times shorter and a solubility 2,500 times higher (50 g/L) than actigall. Table 1 shows a comparison of the formulation of this Example 2 with other formulations.

Example 3

Soluble UDCA Preparation

A clear aqueous solution of solubilized UDCA (s-UDCA) comprising an intact UDCA and an aqueous soluble starch which has low dextrose equivalency was prepared. Briefly, 2.27 g of sodium hydroxide pellets was dissolved in 100 mL of purified water. Next, 25 g of UDCA was dissolved in the sodium hydroxide solution with stirring at room temperature. Separately, 745 g of carbohydrate (maltodextrin) was added portion by portion into 400 mL of purified water and was stirred until dissolved. The resulting clear carbohydrate solution was combined with the sodium salt of UDCA solution and stirred. Into the resulting clear solution, sweetener, preservatives (and/or sweetener and flavoring agents) were added in quantities suitable for a pharmaceutical formulation. The pH of the clear solution was adjusted to 6.5-7.5 with sodium biphosphate. Purified water was added to make total 1000 ml.

The resulting solution was dried in a rotary evaporator at 90-95° C. under vacuum ($1.3 \times 10^{-1}$ Pa) to produce a dry powder form of solubilized UDCA.

Example 4

Experimental Animals and Soluble UDCA Administration

Sixty three Sprague-Dawley male rats weighing ~250 g (Genomics) were anesthetized with ketamine (30 mg/kg)/xylazine hydrochloride (4 mg/kg), and ventilated through a face mask with 20% oxygen. The arterial $P_{CO2}$ was maintained between 35-40 mm Hg and the rectal temperature was controlled and maintained at approximately 37° C. with heating pads. Rats had free access to water but were without food overnight one day before surgery.

Focal middle cerebral artery (MCA) infarctions were induced by intraluminal thread occlusion method. Briefly, an incision was made to expose the left carotid bifurcation. The pterygopalatine branch was identified and ligated. Occlusion of the common carotid artery was achieved with a nylon suture having a silicone-coated tip. This was advanced from the external carotid artery into the lumen of the internal carotid artery until it blocked the origin of the middle cerebral artery (Yanaka et al., 1996, *J. Neurosurg.* 85:125). Cerebral flow was monitored and deemed occluded if flow was reduced

TABLE 1

Pharmacokinetic Parameters of Different UDCA Dosage Forms in Human after Oral Administration

| | Formulation | Base | AUC | Cmax | Tmax |
|---|---|---|---|---|---|
| Simoni et al. | Enteric coated | 500 mg UDCA | 15.3 µg 8 hr mL$^{-1}$ | | |
| Parquet et al. | Capsule | 500 mg UDCA | | 4.43 µg/mL | |
| Panini et al. | 2-Hydroxypropyl-β-cyclodextrin complex | 426 mg UDCA | 8.1 µg 4 hr mL$^{-1}$ | 6.1 µg/mL | 63 min. |
| | Commercial tablets | 450 mg UDCA | 3.8 µg 4 hr mL$^{-1}$ | 2.9 µg/mL | 83 min |
| Example 2 | Liquid formulation with | 500 mg UDCA | 23 µg 4 hr mL$^{-1}$ | 20.4 µg/mL | 15 min |
| | Carbohydrate | 650 mg UDCA | 25.2 µg 4 hr mL$^{-1}$ | 15 µg/mL | 60 min | by 75% relative to baseline. Reperfusion was allowed after 90 minutes by completely removing the suture.

Rats were separated into 5 groups, and each received a single injection of vehicle (n=18), 25 mg s-UDCA/Kg (n=9), 100 mg UDCA/Kg (n=18), 400 mg UDCA/kg (n=9), and 400 mg TUDCA/kg (n=9) intravenously immediately after reperfusion.

During recovery period, rats were assessed for forelimb flexion and contralateral circling to confirm ischemia. No cases of seizure were observed during the experiments at any time following the MCA occlusions. Rectal temperature was maintained at 37±0.5° C. using a feedback-regulated heating system. Free access to food and water was allowed after recovery from anesthesia. Rats were kept in air-ventilated cages at 24±0.5° C. for the period of the experiment. After 2 weeks the amount of pellets was restricted to 30 g/day to control body weight, until 28 days for the efficient Example 5

Bile Acid Analysis of Plasma and Brain

Blood and brain were collected 1 hour after s-UDCA, TUDCA, or vehicle injection, and were assessed by HPLC for bile acid analysis. Briefly, whole blood was drawn, clotted, and centrifuged and plasma was separated and frozen. After appropriate, humane anesthesia (5% chloral hydrate) and transcardial phosphate buffer perfusion, brains were removed, flash-frozen, and stored at −70° C. Free UDCA concentrations were measured by HPLC (JASCO HPLC Bile Acids Analysis System). Bile acids were assessed by HPLC according to, for example, U.S. patent application Ser. No. 09/778,154 filed Feb. 5, 2001, the full disclosure of which is hereby incorporated by reference.

Results are shown in Table 2. Unlike brains of vehicle injected control animals, the UDCA concentration in brains of UDCA-injected animals increased with the amount of s-UDCA injected. Higher UDCA concentrations were observed in brains of animals injected with 25 mg s-UDCA than animals injected with 400 mg TUDCA. No free UDCA was detected in the brains or serum of vehicle-injected control animals.

TABLE 2

HPLC bile analysis results of brain and blood of each group

| s-UDCA per rate body weight | Concentration of free UDCA in Rat Brain Tissues Peek Retention | | Concentration of free UDCA in Rat Blood Peek Retention | |
|---|---|---|---|---|
| | (nmol/g brain) | time (min) | (μmol/L) | time (min) |
| control | 0 | — | 0 | — |
| UDCA 26 mg/Kg | 8.6 | 14.108 | 71.6 | 14.208 |
| UDCA 100 mg/Kg | 9.5 | 14.108 | 165.2 | 14.217 |
| UDCA 400 mg/Kg | 103.6 | 14.258 | 738.1 | 14.242 |
| TUDCA 400 mg/kg | 7.3 | 14.000 | 0 | 14.000 |

Example 6

Behavior Testing

Rotarod test and modified limb placement test (MLPT) were executed at 2 and 7 days after occlusion, as previously described (Jeong et al., 2003, Stroke 34:2258). In brief rats assigned to the behavior test were pre-trained for 3 days in order to alleviate the learning effect in rotarod test (Chen et al., 2001, Stroke 32:1005). In the rotarod test, the rats were placed on the accelerating rotarod cylinder (4-40 rpm), and the time the animals remained on the rotarod was measured three times.

Figure 2B:
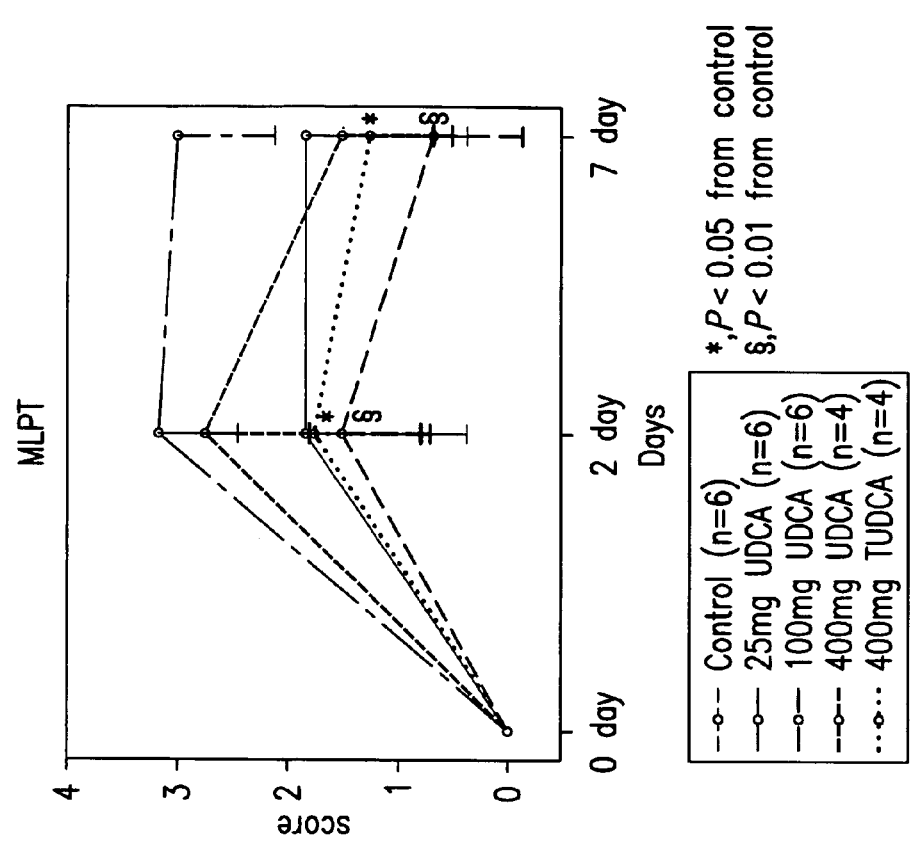
FIG. 2B shows a graphical representation of modified limb placing test (MLPT) results (nine rats were in each group; an asterix ("*") denotes P<0.05, Mann-Whitney U test)
Figure 2A:
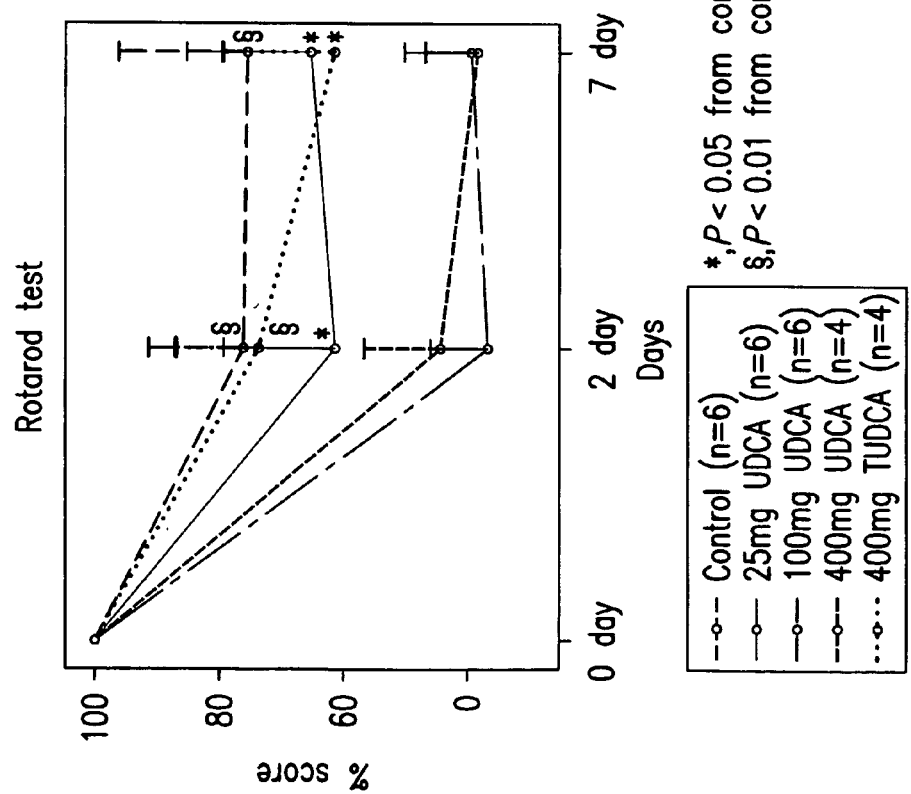
FIG. 2A shows a graphical representation of the of Rotarod test results (nine rats were in each group; an asterix ("*") denotes P<0.05, Mann-Whitney U test)

Rotarod test data are shown in FIG. 2A as percentages of the maximal duration compared with the internal baseline control (before ischemia). When tested on day 7, rats that received vehicle alone remained on the cylinder 36.6% of the baseline time, whereas rats that received 100 mg/kg s-UDCA stayed on for 76.3% of the baseline time.

MLPT consisted of two limb placing tasks that assess the sensorimotor integration of the forelimb and the hind limb, by checking responses to tactile and proprioceptive stimulation (Jeong et al.; Song et al., 2003, Stroke 34:2215). First, each rat was suspended 10 cm over a table and the stretch of the forelimbs towards the table is observed and evaluated: normal stretch, 0 points; abnormal flexion, 1 point. Next, each rat was positioned along the edge of the table, and its forelimbs were placed freely out of the table suspended over the edge and allowed to move freely. Each forelimb (forelimb-second task, hind limb-third task) was gently pulled down and retrieval and placement was checked. Finally, each rat was placed towards the table edge to check for lateral placement of the forelimb. The three tasks were scored in the following manner: normal performance, 0 points; performance with a delay (2 s) and/or incomplete, 1 point; no performance, 2 points; 7 points means maximal neurological deficit and 0 points means normal performance. Results are shown in FIG. 2B. Animals that received vehicle alone scored 3.2 while rats that received 100 mg/kg s-UDCA scored 1.5.

Animals treated with s-UDCA performed better than control animals. In addition, animals in the 100 mg UDCA group showed significantly better performance than 25 mg UDCA and 400 mg TUDCA groups. The 100 mg s-UDCA treated group showed best performance on the Rotarod and MLPT after 7 days, to a lesser extent in 25 mg s-UDCA and 400 mg TUDCA group, compared with control group (FIG. 2). At 28 days after reperfusion, the Rotarod performance showed 80% improvement of pretrained level, whereas the vehicle-injected control group showed 40% (data not shown). The initial body weight and those over the course of 4 weeks were similar.

Example 7

Infarction Volume

After behavioral tests, brains were removed, and 1 mm thick serial sections through the entire brain were cut using a brain matrix device. Each section was subsequently stained with Nissl. Cortical, striatal as well as hemispheric volume in the infarcted and contralesional areas of each section were traced and measured using an image analysis system (Image-Pro Plus™, Media Cybernetics, Silver Spring, Md.). Quantification of the extent of injury was determined by using a computerized image analysis system. To accomplish this, a digital image of each section was obtained and the area of injury delineated by outlining the region in which Nissl was not reduced. For cases in which the necrosis was so severe that tissue was actually lost and therefore the borders could not be directly assessed, an outline of the contralateral side was used to estimate the volume of injured brain. Total volume of infarct was calculated by the Cavalieri method.

Figure 1A:
FIG. 1A shows coronal sections of rat brains stained with Nissl.

A well-defined pale area, considered to be infarct, may be seen in the left hemisphere (FIG. 1A). The infarct volumes at 2 days were markedly reduced in animals that received 100 mg s-UDCA, especially in the cortex (FIG. 1A).

The mean infarct volumes of the 100 mg s-UDCA treated group at 2 days (41.03±29.2 mm$^3$) were less than half of vehicle-injected infarct (90.59±33.03 mm$^3$, P<0.05) (FIG. 1B). Similar results were observed at 7 days after reperfusion; 86.64±18.78 mm$^3$ in control group, 39.07±26.36 mm$^3$ in 25 mg s-UDCA group, 26.87±26.63 mm$^3$ in 100 mg UDCA group (FIG. 1B). While the infarct volume of animals in the 400 mg s-UDCA group was less than animals in the control group, the difference in this particular experiment may not have been statistically significant.

Example 8

TUNEL Staining

At 2 and 7 days after reperfusion, apoptotic cells were quantified by using the TUNEL assay. TUNEL was accomplished using a DNA fragmentation detection kit (cat. no. QIA33; Oncogene, Boston, Mass., USA). After immersion in 100 µl of 3% $H_2O_2$ for 5 min, sections were incubated in a TdT labeling reaction mixture (supplied with kit) in a humidified chamber for 90 min at 37 C, and then incubated in the stop buffer at 37° C. for 5 min. Sections were washed with PBS before being incubated in blocking buffer (supplied with kit) for 30 min at room temperature, colored with diaminobenzidine-$H_2O_2$ solution, and counterstained with methyl green. According to morphologic criteria, TUNEL-positive nuclei with chromatin condensation and fragmented nuclei were considered as probable apoptotic cells, and TUNEL-positive cells with diffuse light brown labeling of nucleus and cytoplasm were considered probable necrotic cells.

Quantitative examinations were made in TUNEL staining. The lateral caudoputamen and the upper frontoparietal cortex were selected for analysis, because these two areas are typically affected by the ischemic injury, and represent different extents of cortical brain function reduction. It is likely that the lateral caudoputamen contains the ischemic core and the frontoparietal cortex the boundary zone or penumbra, in this MCA occlusion model. Five non-overlapping microscopic fields per region per section and two sections per brain were analyzed by a blinded investigator. The number of apoptotic cells in each region was counted in a high-power field (×400), and this was expressed as number/mm$^2$.

Figure 3A:
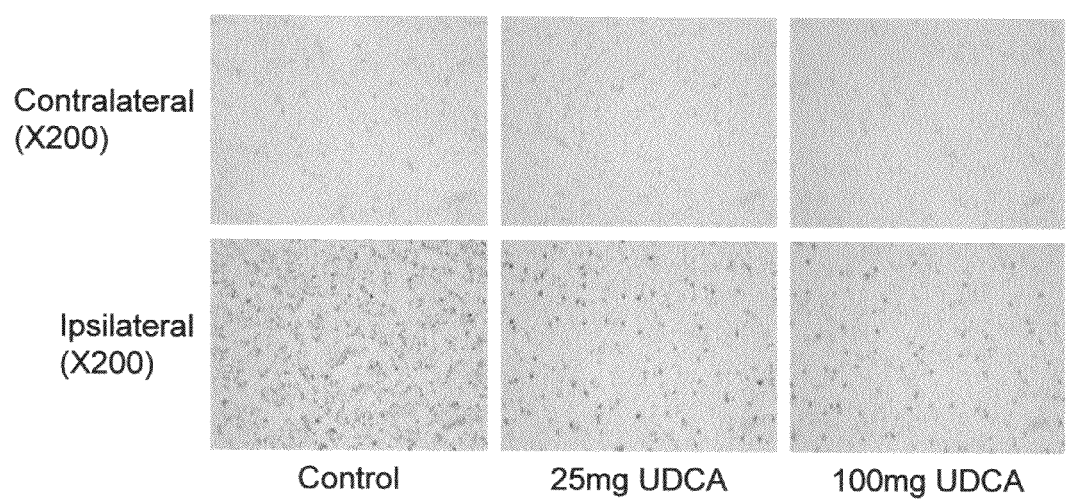
FIG. 3A shows micrographs of cells in the ischemic penumbra following TUNEL labeling.
Figure 3B:
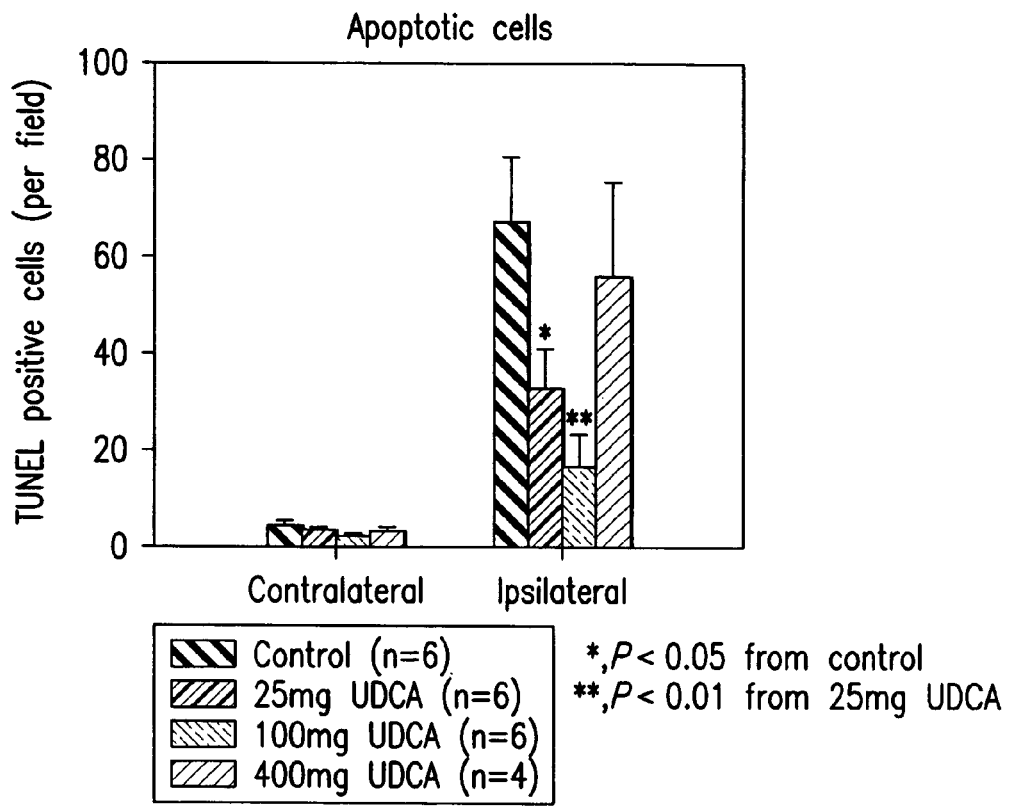
FIG. 3B shows a graphical representation of the number of TUNEL positive cells per field in the contralateral and ipsilateral hemispheres (data are presented as means±S.D. (bars) values)

Micrographs of labeled tissue are shown in FIG. 3A and a results chart is shown in FIG. 3B.

As shown in FIG. 3A, TUNEL-positive apoptotic cells were detected in the lateral caudoputamen and frontoparietal cortex of all groups 7 days after reperfusion (FIG. 3A). These results indicate that 25 mg and 100 mg s-UDCA significantly reduced the number of TUNEL-positive cells in the hemisphere ipsilateral to MCA occlusion.

Quantitative analysis showed about 50% reduction of apoptotic cells after 25 mg s-UDCA group. In addition, when administered at higher dosage, 100 mg s-UDCA, reduction of apoptotic cell reached to about 70%. Specifically, vehicle control rats were observed to have 67.5 TUNEL-positive cells (hits) per field (FIG. 3B) and by contrast, rats that received 100 mg/kg s-UDCA were observed to have 16.7 hits per field (HFP). Apoptotic cells were statistically examined using the Student's t-test.

Example 9

Caspase Activity

On day 7 after reperfusion, whole brains were homogenized in isolation buffer and were assessed for DEVD-specific caspase activity to be immediately placed in lysis buffer (5 mM Tris-HCl, pH 7.4, 20 mM EDTA and 0.5% Triton-X 100) at 4° C. for 15 min. The lysates were then centrifuged at 1000 g for 10 min at 4 C, and supernatants were centrifuged at 17,000 g for 20 min at 4 C. Protein concentrations were determined using the Bradford method (Bio-Rad, Richmond, Calif., USA). Ac-DEVD-AMC [N-acetyl-Asp-Glu-Val-Asp-AMP (7-amino-4-methylcoumarin)] (Pharmingen, San Diego, Calif., USA) was used for the caspase-3 activity assays, and 200 µg of protein, 200 µl of reaction buffer (20 mM HEPES, pH 7.5, 10% glycerol, 4 mM DTT), and 5 µl (1 µg/µl) of reconstituted Ac-DEVD-AMC were added to each well of a 96-well plate. The reaction mixture was incubated for 1 hour at 37 C. The amount of AMC released was measured using a fluorescence spectrophotometer (LS-50B, Perkin-Elmer, Wellesley, Mass., USA) at 380 nm excitation and 460 nm emission.

Figure 3C:
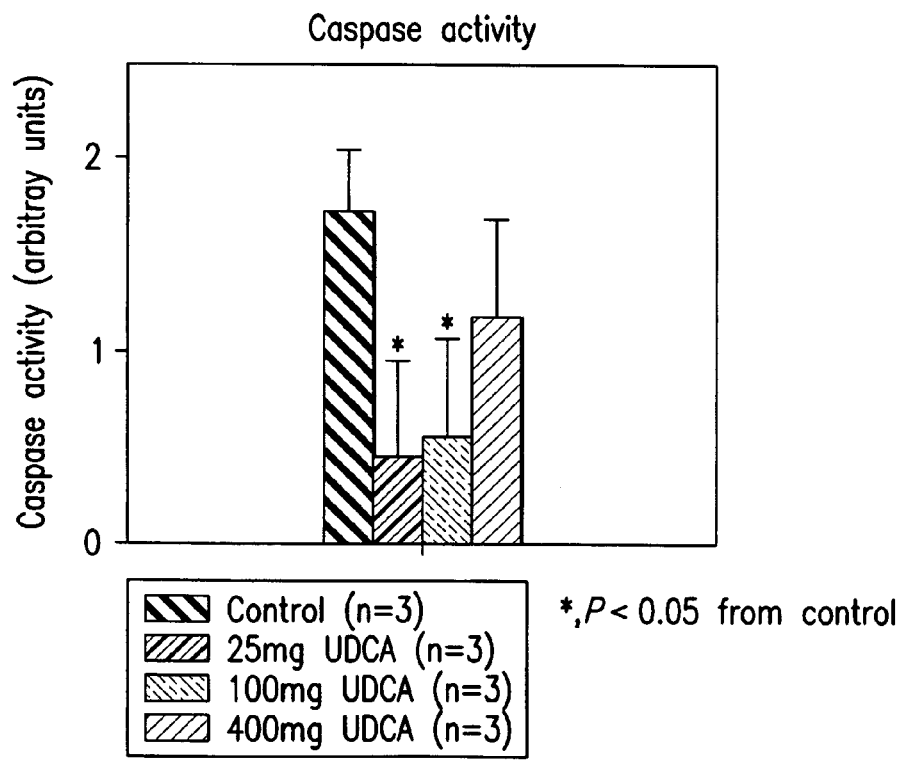
FIG. 3C shows a graphical representation of the caspase activity (in arbitrary units) observed in each treatment group (data are expressed as means±S.D.)

The results in FIG. 3C show that s-UDCA also prevented activation of caspase-3, which was measured using the colorimetric substrates DEVD-pNA. 25 mg and 100 mg s-UDCA group showed decreased caspase-3 activity at 7 days after reperfusion. An asterix ("*") denotes P<0.05, which constitutes a significant difference between the control and the postischemic groups as analyzed by ANOVA followed by Fisher's protected least significant difference test. Caspase-3 activity was found to be significantly decreased 7 days after reperfusion in the 100 mg s-UDCA group (1.72±0.32, n=3), compared with control group (0.56±0.51, n=3). Caspase activity was also reduced in animals injected with 25 mg s-UDCA or 400 mg s-UDCA, although the reduction with 400 mg s-UDCA may not have been statistically significant in this one example.

Example 10

Western Blot Analysis

Figure 4:
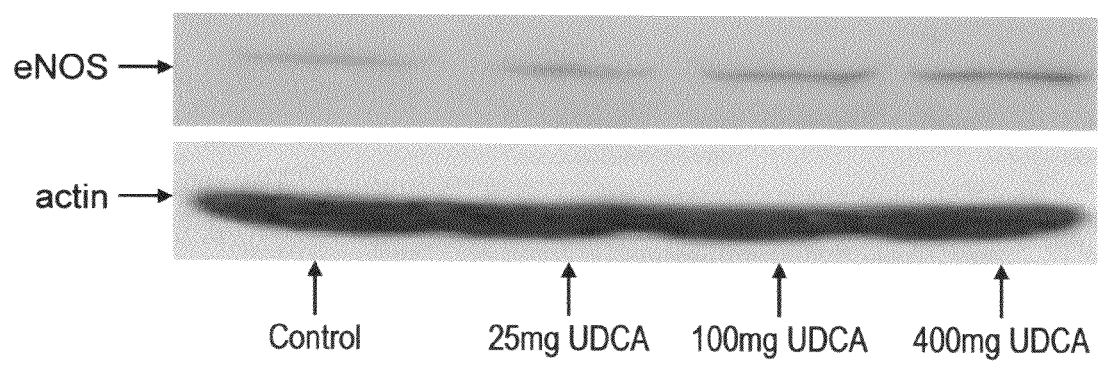
FIG. 4 shows eNOS expression measured by Western blot analysis.

To further evaluate any neuroprotective effect, eNOS expression was assessed by Western blot at 7 days after reperfusion. Results are shown in FIG. 4.

Without being limited to any mechanism of action, the foregoing results may show that s-UDCA may reduce infarction volume and enhance functional recovery after ischemic stroke through inhibition of apoptosis and enhancement eNOS expression. In some embodiments, a 100 mg UDCA/kg dose may be more effective, while a 400 mg UDCA/kg dose may be associated with higher mortality. In some specific example embodiments, increased solution viscosity due to maltodextrin may relate to increased mortality. According to some embodiments, s-UDCA may correlate with UDCA concentration in brain and blood. TUDCA, however, was not detected in brain as well as blood after UDCA and TUDCA administration although the UDCA concentration was mildly increased in brain after TUDCA injection.

Example 11

Physiologic Parameters

All animals of control, 25 mg, 100 mg s-UDCA group survived the surgery after 1 week. But, the 400 mg s-UDCA group showed frequent dyspnea and death (75% mortality rate) probably due to vascular plugging by intravenous injection of viscous s-UDCA solution, which was confirmed by autopsy. Among the surviving animals, the physiologic parameters, including mean arterial blood pressure, blood gases, serum glucose, and body temperature, were not significantly different in any experimental groups before, during, or after infarction.

Example 12

Statistical Analysis

Data are presented as means±S.D. Statistical analyses of the physiologic variables were performed using one-way analysis of variance. Student's t-test was used to determine the significance of any differences in the volume of infarction and the number of apoptotic cells between the groups. The levels of caspase-3 activity were examined by analysis of variance followed by Fisher's protected least significant difference test. A P value of <0.05 was considered significant.

What is claimed is:

1. A method of reducing infarction volume of an ischemic stroke in a subject having an ischemic stroke, said method comprising: administering to the subject a composition comprising:
   (a) a bile acid material selected from the group consisting of an ursodeoxycholic acid, an aqueous soluble halo- and/or amino-derivative of an ursodeoxycholic acid, and an ursodeoxycholic acid salt;
   (b) a carbohydrate selected from the group consisting of an aqueous soluble starch conversion product having at least one reducing end or at least one non-reducing end and an aqueous soluble non-starch polysaccharide; and
   (c) water,
   wherein (1) the bile acid material and the carbohydrate both remain in solution for all pH values of the solution between about pH 1 and about pH 14, (2) the bile acid material is at a dosage so that the subject receives from about 25 mg/kg to about 100 mg/kg, (3) the administering comprises administering by a route selected from the group consisting of orally administering, sublingually administering, parenterally administering, intradermally injecting, subcutaneously injecting, intrathyroidally injecting, intravenously injecting, intranasally administering, transdermally administering, and transconjunctivally administering, and (4) infarction volume is reduced.

2. A method of enhancing functional recovery in a subject having an ischemic stroke, said method comprising: administering to the subject a composition comprising:
   (a) a bile acid material selected from the group consisting of an ursodeoxycholic acid, an aqueous soluble halo- and/or amino-derivative of an ursodeoxycholic acid, and an ursodeoxycholic acid salt;
   (b) a carbohydrate selected from the group consisting of an aqueous soluble starch conversion product having at least one reducing end or at least one non-reducing end and an aqueous soluble non-starch polysaccharide; and
   (c) water,
   wherein (1) the bile acid material and the carbohydrate both remain in solution for all pH values of the solution between about pH 1 and about pH 14, (2) the bile acid material is at a dosage so that the subject receives from about 25 mg/kg to about 100 mg/kg, (3) the administering comprises administering by a route selected from the group consisting of orally administering, sublingually administering, parenterally administering, intradermally injecting, subcutaneously injecting, intrathyroidally injecting, intravenously injecting, intranasally administering, transdermally administering, and transconjunctivally administering, and (4) functional recovery is improved.

3. A method of increasing the expression of eNOS in a subject having an ischemic stroke, said method comprising: administering to the ischemic stroke subject a composition comprising:
   (a) a bile acid material selected from the group consisting of an ursodeoxycholic acid, an aqueous soluble halo- and/or amino-derivative of an ursodeoxycholic acid, and an ursodeoxycholic acid salt;
   (b) a carbohydrate selected from the group consisting of an aqueous soluble starch conversion product having at least one reducing end or at least one non-reducing end and an aqueous soluble non-starch polysaccharide; and
   (c) water,
   wherein (1) the bile acid material and the carbohydrate both remain in solution for all pH values of the solution between about pH 1 and about pH 14, (2) the bile acid material is at a dosage so that the subject receives from about 25 mg/kg to about 100 mg/kg, (3) the administering comprises administering by a route selected from the group consisting of orally administering, sublingually administering, parenterally administering, intradermally injecting, subcutaneously injecting, intrathyroidally injecting, intravenously injecting, intranasally administering, transdermally administering, and transconjunctivally administering, and (4) eNOS expression is increased.

4. A method of inhibiting apoptosis and increasing the expression of eNOS in a subject having an ischemic stroke, said method comprising: administering to the ischemic stroke subject a composition comprising:
   (a) a bile acid material selected from the group consisting of an ursodeoxycholic acid, an aqueous soluble halo- and/or amino-derivative of an ursodeoxycholic acid, and an ursodeoxycholic acid salt;
   (b) a carbohydrate selected from the group consisting of an aqueous soluble starch conversion product having at least one reducing end or at least one non-reducing end and an aqueous soluble non-starch polysaccharide; and
   (c) water,
   wherein (1) the bile acid material and the carbohydrate both remain in solution for all pH values of the solution between about pH 1 and about pH 14, (2) the bile acid material is at a dosage so that the subject receives from about 25 mg/kg to about 100 mg/kg, (3) the administering comprises administering by a route selected from the group consisting of orally administering, sublingually administering, parenterally administering, intradermally injecting, subcutaneously injecting, intrathyroidally injecting, intravenously injecting, intranasally administering, transdermally administering, and transconjunctivally administering, and (4) apoptosis is reduced and eNOS expression is increased.

5. A method of treating at least one symptom of ischemic stroke in a subject having an ischemic stroke, said method comprising: administering to the subject a composition comprising:
   (a) a bile acid material selected from the group consisting of an ursodeoxycholic acid, an aqueous soluble halo- and/or amino-derivative of an ursodeoxycholic acid, and an ursodeoxycholic acid salt;
   (b) a carbohydrate selected from the group consisting of an aqueous soluble starch conversion product having at least one reducing end or at least one non-reducing end and an aqueous soluble non-starch polysaccharide; and
   (c) water,
   wherein (1) the bile acid material and the carbohydrate both remain in solution for all pH values of the solution between about pH 1 and about pH 14, (2) the bile acid material is at a dosage so that the subject receives from about 25 mg/kg to about 100 mg/kg, (3) the administering comprises administering by a route selected from the group consisting of orally administering, sublingually administering, parenterally administering, intradermally injecting, subcutaneously injecting, intrathyroidally injecting, intravenously injecting, intranasally administering, transdermally administering, and transconjunctivally administering, and (4) at least one symptom of ischemic stroke is treated.

6. A method of delivering a bile acid material to the brain in a subject having an ischemic stroke comprising: administering to the subject a composition comprising:
(a) a bile acid material selected from the group consisting of an ursodeoxycholic acid, an aqueous soluble halo- and/or amino-derivative of an ursodeoxycholic acid, and an ursodeoxycholic acid salt;
(b) a carbohydrate selected from the group consisting of an aqueous soluble starch conversion product having at least one reducing end or at least one non-reducing end and an aqueous soluble non-starch polysaccharide; and
(c) water,
wherein (1) the bile acid material and the carbohydrate both remain in solution for all pH values of the solution between about pH 1 and about pH 14, (2) the bile acid material is at a dosage so that the subject receives from about 25 mg/kg to about 100 mg/kg, (3) the administering comprises administering by a route selected from the group consisting of orally administering, sublingually administering, parenterally administering, intradermally injecting, subcutaneously injecting, intrathyroidally injecting, intravenously injecting, intranasally administering, transdermally administering, and transconjunctivally administering, and (4) a bile acid material is delivered to the brain.

7. A method according to any one of claims 1-6, wherein the composition further comprises at least one pharmaceutical selected from the group consisting of anisindion, dicumarol, warfarin sodium, citrate dextrose solution, aminocaproic acid, tranexamic acid, ticlopidine HCl, clopidogrel bisulfate, eptifibatide, tirofiban HCL, amlodipine salts, bepridil HCL, diltiazem HCL, felodipine, Nifedipine, betamethasone, dexamethasone, fludrocortisone, flunisolide, hydrocortisone, mecamylamine HCl, trimethaphan camsylate, erythropoietin, a granulocyte colony stimulating factor, microfibrillar collagen, absorbable gelatin, thrombin, L-arginine, abciximab, alteplase, streptokinase, urokinase, diazoxide, hydralazine HCl, minoxidil, dan Shen, dengzhanhua, didang tang, lubeluzole, mannitol solution, naftidrofury, pentoxifylline, propentofylline, pentifylline piracetam, prostacyclin, puerarin, sanchi, theophylline, aminophylline, tirilazad, triflusal, and vinpocetin.

8. A method according to any one of claims 1-6, wherein the composition is a clear solution.

9. A method according to any one of claims 1-6, wherein the bile acid material is ursodeoxycholic acid.

10. A method according to claim 9, wherein the composition is a dried solubilized ursodeoxycholic acid formulation.

11. A method according to any one of claims 1-6, wherein the subject is a non-human mammal.

12. A method according to any one of claims 1-6, wherein the subject is a human.

13. A method according to any one of claims 1-6, wherein the composition is free of cyclodextrin.

14. A method according to any one of claims 1-6, wherein the carbohydrate comprises an aqueous soluble starch conversion product having at least one reducing end or at least one non-reducing end selected from the group consisting of maltodextrin, dextrin, liquid glucose, corn syrup solid, and soluble starch.

\* \* \* \* \*